US012678043B2

(12) United States Patent
Shimosawa et al.

(10) Patent No.: US 12,678,043 B2
(45) Date of Patent: Jul. 14, 2026

(54) OPHTHALMIC APPARATUS, METHOD OF CONTROLLING SAME, AND RECORDING MEDIUM

(71) Applicant: Topcon Corporation, Tokyo (JP)

(72) Inventors: Ryosuke Shimosawa, Tokyo (JP); Kazuhiro Yamada, Tokyo (JP); Masaya Suzuki, Tokyo (JP)

(73) Assignee: TOPCON CORPORATION, Tokyo (JP)

( * ) Notice: Subject to any disclaimer, the term of this patent is extended or adjusted under 35 U.S.C. 154(b) by 973 days.

(21) Appl. No.: 17/945,138

(22) Filed: Sep. 15, 2022

(65) Prior Publication Data

US 2023/0014194 A1 Jan. 19, 2023

Related U.S. Application Data

(63) Continuation of application No. PCT/JP2021/008666, filed on Mar. 5, 2021.

(30) Foreign Application Priority Data

Mar. 19, 2020 (JP) ................................ 2020-048736

(51) Int. Cl.
*A61B 3/10* (2006.01)
*A61B 3/00* (2006.01)
(Continued)

(52) U.S. Cl.
CPC .............. *A61B 3/14* (2013.01); *A61B 3/0008* (2013.01); *A61B 3/0025* (2013.01); *A61B 3/113* (2013.01);
(Continued)

(58) Field of Classification Search
CPC ......... A61B 3/102; A61B 3/1025; A61B 3/02; A61B 3/113; A61B 3/1015; A61B 3/1225;
(Continued)

(56) References Cited

U.S. PATENT DOCUMENTS 4,732,466 A 3/1988 Humphrey
5,028,802 A 7/1991 Webb et al.
(Continued)

FOREIGN PATENT DOCUMENTS

JP S61-293430 A 12/1986
JP 2007090120 A 4/2007
(Continued)

OTHER PUBLICATIONS

Chinese Office Action issued Apr. 24, 2025, in Chinese Patent Application No. 202180021987.3, 15pp.
(Continued)

*Primary Examiner* — Dawayne Pinkney
(74) *Attorney, Agent, or Firm* — XSENSUS LLP

(57) ABSTRACT

An ophthalmic apparatus includes an illumination optical system that generates slit-shaped illumination light using a first light source; an optical scanner that deflects the illumination light to a fundus of a subject's eye; an imaging optical system that captures light from the fundus using a rolling shutter method; an acquisition unit that acquires a fundus image of the subject's eye using light from a second light source; a flare determination unit that determines whether or not flare occurs by analyzing the fundus image; a controller that performs flare optimization control by controlling at least one of the first light source, the illumination optical system, the optical scanner, the imaging optical system, and the image sensor based on a first determination result obtained by the flare determination unit; and an image
(Continued)

forming unit that forms an image of the fundus when the flare does not occur.

19 Claims, 14 Drawing Sheets

(51) Int. Cl.

| | |
|---|---|
| *A61B 3/02* | (2006.01) |
| *A61B 3/113* | (2006.01) |
| *A61B 3/12* | (2006.01) |
| *A61B 3/14* | (2006.01) |
| *G06T 7/00* | (2017.01) |

(52) U.S. Cl.
CPC .............. *A61B 3/12* (2013.01); *G06T 7/0012* (2013.01); *G06T 2207/30041* (2013.01)

(58) Field of Classification Search
CPC ..... A61B 3/0083; A61B 3/0058; A61B 3/024; A61B 3/15; A61B 3/135; A61B 3/0025; A61B 3/1005; A61B 3/152; A61B 3/14; A61B 3/0008; A61B 3/0016; A61B 3/12
USPC ....... 351/206, 205, 200, 209, 210, 221–223, 351/245–246
See application file for complete search history.

(56) References Cited

U.S. PATENT DOCUMENTS

| | | | |
|---|---|---|---|
| 5,949,520 A | 9/1999 | Heacock | |
| 7,831,106 B2 | 11/2010 | Elsner et al. | |
| 8,237,835 B1 | 8/2012 | Muller | |
| 2010/0057059 A1 | 3/2010 | Makino | |
| 2012/0050674 A1* | 3/2012 | Ota | A61B 3/12 |
| | | | 351/246 |
| 2012/0242955 A1* | 9/2012 | Yoshino | A61B 3/0091 |
| | | | 351/208 |
| 2012/0249956 A1* | 10/2012 | Narasimha-Iyer ... | A61B 5/0066 |
| | | | 351/246 |
| 2013/0222763 A1 | 8/2013 | Bublitz et al. | |
| 2013/0229620 A1 | 9/2013 | Hammer et al. | |
| 2014/0028976 A1* | 1/2014 | Tanassi | A61B 3/152 |
| | | | 351/208 |
| 2015/0085252 A1 | 3/2015 | Fujimura et al. | |
| 2015/0131050 A1 | 5/2015 | Bublitz et al. | |
| 2015/0272438 A1 | 10/2015 | Yao et al. | |
| 2016/0345822 A1 | 12/2016 | Fujimura et al. | |
| 2019/0282092 A1* | 9/2019 | Nakamura | A61B 3/0083 |
| 2019/0282093 A1 | 9/2019 | Nakamura | |
| 2020/0000335 A1* | 1/2020 | Yoshino | A61B 3/152 |

FOREIGN PATENT DOCUMENTS

| | | | |
|---|---|---|---|
| JP | 2009112665 A | 5/2009 | |
| JP | 2009-172158 A | 8/2009 | |
| JP | 2010-259495 A | 11/2010 | |
| JP | 2013-248376 A | 12/2013 | |
| JP | 2016185192 A | 10/2016 | |
| JP | 2019-155002 A | 9/2019 | |
| JP | 2020006172 A | 1/2020 | |
| WO | 2008/066135 A1 | 6/2008 | |
| WO | 2012/059236 A1 | 5/2012 | |

OTHER PUBLICATIONS

Extended European Search Report issued Feb. 27, 2024, in corresponding European Patent Application No. 21770445.1, 12pp.
International Search Report and Written Opinion mailed on Apr. 6, 2021, received for PCT Application PCT/JP2021/008666, Filed on Mar. 5, 2021, 8 pages including English Translation.
Chinese Office Action issued Oct. 13, 2025, in corresponding Chinese Patent Application No. 202180021987.3, 13pp.

* cited by examiner

OPHTHALMIC APPARATUS, METHOD OF CONTROLLING SAME, AND RECORDING MEDIUM

CROSS-REFERENCE TO RELATED APPLICATIONS

The present application is a continuation application of International Patent Application No. PCT/JP2021/008666, filed Mar. 5, 2021, which claims priority to Japanese Patent Application No. 2020-048736, filed Mar. 19, 2020, both of which are herein incorporated by reference in their entirety.

FIELD

The disclosure relates to an ophthalmic apparatus, a method of controlling the same, and a program.

BACKGROUND

In recent years, screening tests have been performed using ophthalmic apparatuses. Such ophthalmic apparatuses are expected to be applied to self-examinations, and further downsizing and weight saving of the ophthalmic apparatuses are desired.

For example, U.S. Pat. Nos. 7,831,106 and 8,237,835 disclose ophthalmic apparatuses configured to pattern-illuminate a subject's eye and to receive returning light thereof using an image sensor, using a rolling shutter method. These ophthalmic apparatuses can acquire images of the subject's eye with a simple configuration, by adjusting the illumination pattern and the timing of light receiving timing using the image sensor.

SUMMARY

One aspect of some embodiments is an ophthalmic apparatus, including: a first light source; an illumination optical system configured to generate slit-shaped illumination light using light from the first light source; an optical scanner configured to deflect the illumination light to guide the illumination light to a fundus of a subject's eye; an imaging optical system configured to guide returning light of the illumination light from the fundus to an image sensor, the image sensor being configured to capture light receiving result of the returning light using a rolling shutter method, the light receiving result corresponding to an irradiated position of the illumination on the fundus; an acquisition unit configured to acquire a fundus image of the subject's eye using light from a second light source; a flare determination unit configured to determine whether or not flare occurs, by analyzing the fundus image of the subject's eye; a controller configured to perform flare optimization control in which an imaging condition is changed so as to eliminate an occurrence of the flare, by controlling at least one of the first light source, the illumination optical system, the optical scanner, the imaging optical system, and the image sensor based on a first determination result obtained by the flare determination unit; and an image forming unit configured to form an image of the fundus based on the light receiving result captured by the image sensor, when it is determined that the flare does not occur, based on a second determination result obtained by the flare determination unit using the fundus image acquired by the acquisition unit under the imaging condition changed by performing the flare optimization control.

Another aspect of some embodiments is an method of controlling an ophthalmic apparatus including: a first light source; and an illumination optical system configured to generate slit-shaped illumination light using light from the first light source; an optical scanner configured to deflect the illumination light to guide the illumination light to a fundus of a subject's eye; an imaging optical system configured to guide returning light of the illumination light from the fundus to an image sensor, the image sensor being configured to capture light receiving result of the returning light, the light receiving result corresponding to an irradiated position of the illumination on the fundus; and an acquisition unit configured to acquire a fundus image of the subject's eye using light from a second light source. The method of controlling the ophthalmic apparatus includes: a first flare determination step of determining whether or not flare occurs, by analyzing the fundus image of the subject's eye; a control step of performing flare optimization control in which an imaging condition is changed so as to eliminate an occurrence of the flare, by controlling at least one of the first light source, the illumination optical system, the optical scanner, the imaging optical system, and the image sensor based on a first determination result obtained in the first flare determination step; a second flare determination step of determining whether or not flare occurs, by analyzing the fundus image acquired by the acquisition unit under the imaging condition changed by performing the flare optimization control; and an image forming step of forming an image of the fundus based on the light receiving result captured by the image sensor, when it is determined, based on a second determination result obtained in the second flare determination step, that the flare does not occur.

Still another aspect of some embodiments is a non-transitory computer readable recording medium storing a program of causing a computer to execute each step of the method of controlling the ophthalmic apparatus described above.

DETAILED DESCRIPTION

Figure 1:
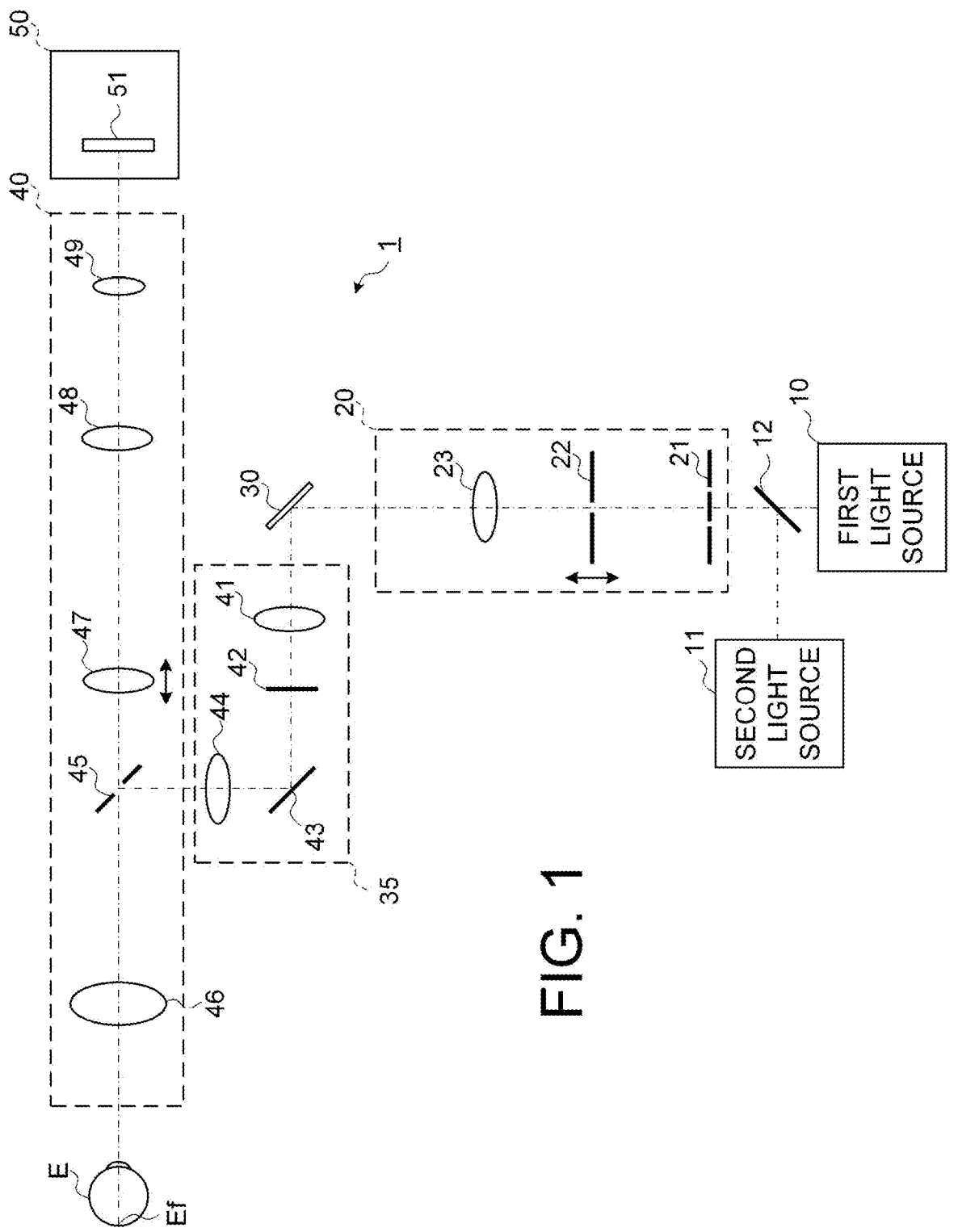
FIG. 1 is a schematic diagram illustrating an example of a configuration of an optical system of an ophthalmic apparatus according to embodiments.

Images of the subject's eye may occur so-called flares. In general, it is effective to reduce light amount of illumination light for reducing flare.

However, in this type of ophthalmic device, the light amount of the illumination light and an imaging time have a trade-off relationship. Specifically, when the light amount of the illumination light is reduced, it is necessary to lengthen the imaging time to compensate for the reduced light amount. However, as the imaging time is lengthened, the image quality deteriorates due to the involuntary eye movement of the subject's eye, etc. during imaging. In contrast, when the light amount of the illumination light is increased, the imaging time can be shortened. However, as the light amount increases, the flare is more likely to occur.

The ease of occurrence of such flares varies from subject's eye to subject's eye. Therefore, it is very difficult to obtain high quality images of the subject's eye while suppressing flares that occur in different ways for each subject's eye.

According to some embodiments according to the present invention, a new technique for acquiring a high quality image of a subject's eye while suppressing flares can be provided.

Referring now to the drawings, exemplary embodiments of an ophthalmic apparatus, a method of controlling the same, and a program according to the present invention are described below. The contents of the document cited in the present specification can be appropriately incorporated as contents of the following embodiments.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

An ophthalmic apparatus according to embodiments illuminates a predetermined site of a subject's eye while moving an irradiated position (illumination region, irradiated range) of slit-shaped illumination light, and receives returning light from the predetermined site using an image sensor with a one-dimensional or two-dimensional array of light receiving elements. Light receiving result of the returning light is read out from the light receiving element(s) at light receiving position of the returning light corresponding to the irradiated position of the illumination light, in synchronization with the movement timing of the irradiated position of the illumination light. In some embodiments, the predetermined site is an anterior segment or a posterior segment. Examples of the anterior segment include a cornea, an iris, a crystalline lens, a ciliary body, and a ciliary zonule. Examples of the posterior segment include a vitreous body, and a fundus or the vicinity of the fundus (retina, choroid, sclera, etc.).

A method of controlling the ophthalmic apparatus according to the embodiments includes one or more steps for realizing the processing executed by a processor (computer) in the ophthalmic apparatus according to the embodiments. A program according to the embodiments causes the processor to execute each step of the method of controlling the ophthalmic apparatus according to the embodiments.

The term "processor" as used herein refers to a circuit such as, for example, a central processing unit (CPU), a graphics processing unit (GPU), an application specific integrated circuit (ASIC), and a programmable logic device (PLD). Examples of PLD include a simple programmable logic device (SPLD), a complex programmable logic device (CPLD), and a field programmable gate array (FPGA). The processor realizes, for example, the function according to the embodiments by reading out a computer program stored in a storage circuit or a storage device and executing the computer program.

Hereinafter, a case where the ophthalmic apparatus according to the embodiments acquires images of the fundus of the subject's eye mainly will be described. In the following, unless otherwise mentioned, an imaging time (shooting time, image capture time, time required for imaging) using an image sensor is assumed to correspond to an exposure time at a light receiving element of the image sensor, and "imaging time" and "exposure time" are sometimes used interchangeably.

[Configuration of Optical System]

Figure 2:
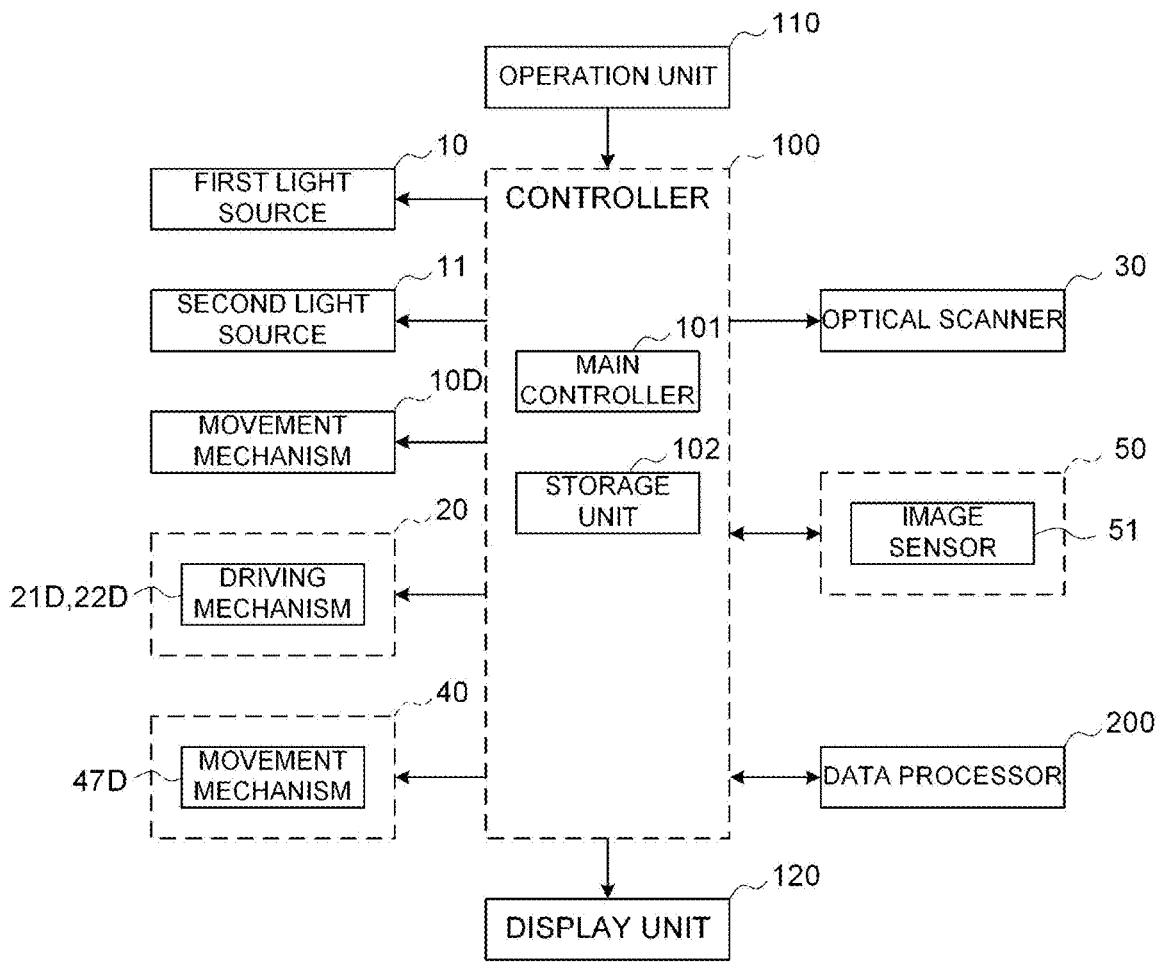
FIG. 2 is a schematic diagram illustrating an example of a configuration of a control system of the ophthalmic apparatus according to the embodiments.
Figure 3:
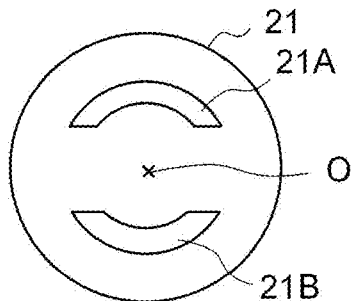
FIG. 3 is a schematic diagram illustrating an example of a configuration of an optical system of the ophthalmic apparatus according to the embodiments.
Figure 4A:
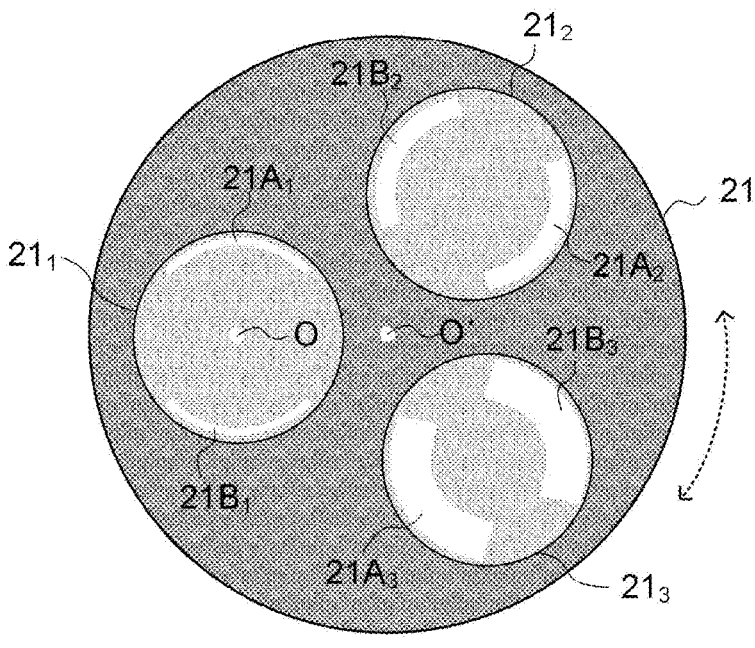
FIG. 4A is a schematic diagram illustrating an example of a configuration of an optical system of the ophthalmic apparatus according to the embodiments.
Figure 4B:
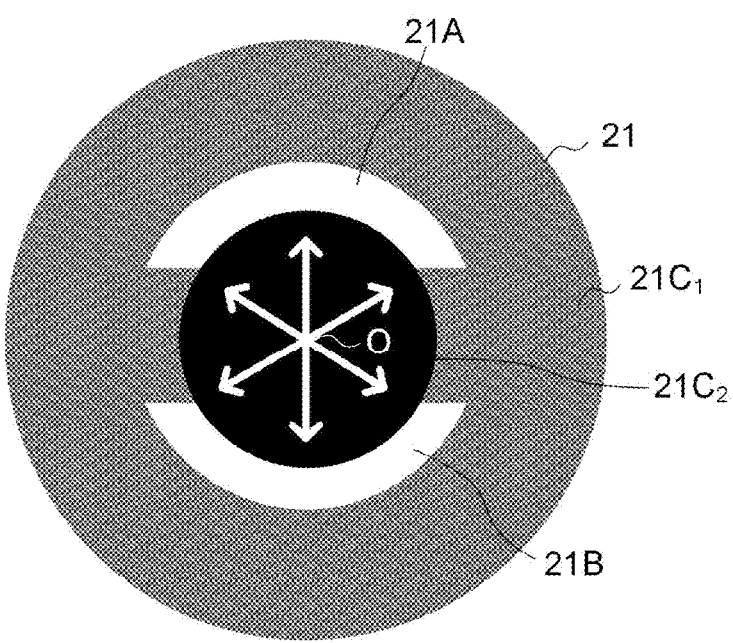
FIG. 4B is a schematic diagram illustrating an example of a configuration of an optical system of the ophthalmic apparatus according to the embodiments.
Figure 5A:
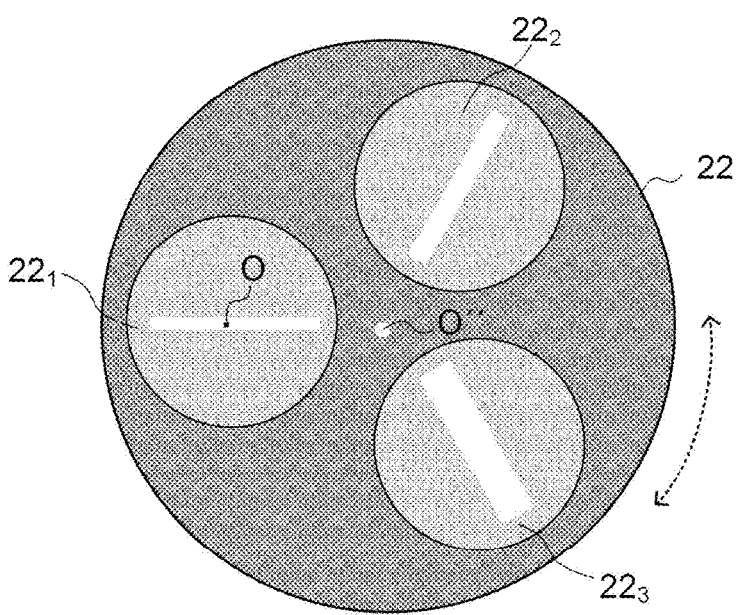
FIG. 5A is a schematic diagram illustrating an example of a configuration of an optical system of the ophthalmic apparatus according to the embodiments.
Figure 5B:
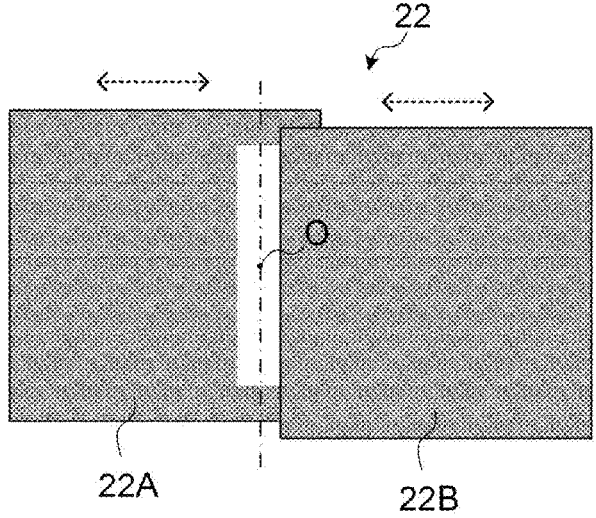
FIG. 5B is a schematic diagram illustrating an example of a configuration of an optical system of the ophthalmic apparatus according to the embodiments.
Figure 6:
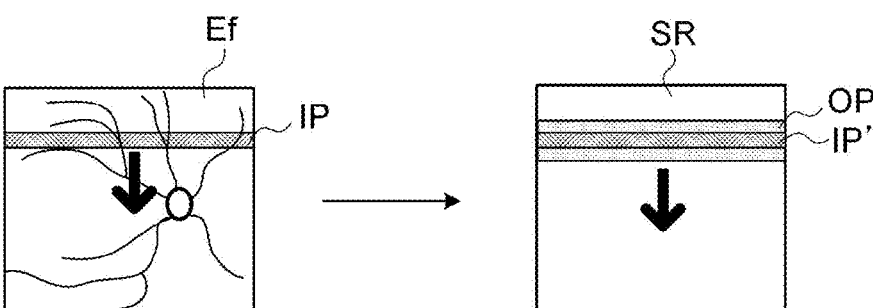
FIG. 6 is an explanatory diagram of the operation of the ophthalmic apparatus according to the embodiments.
Figure 7:
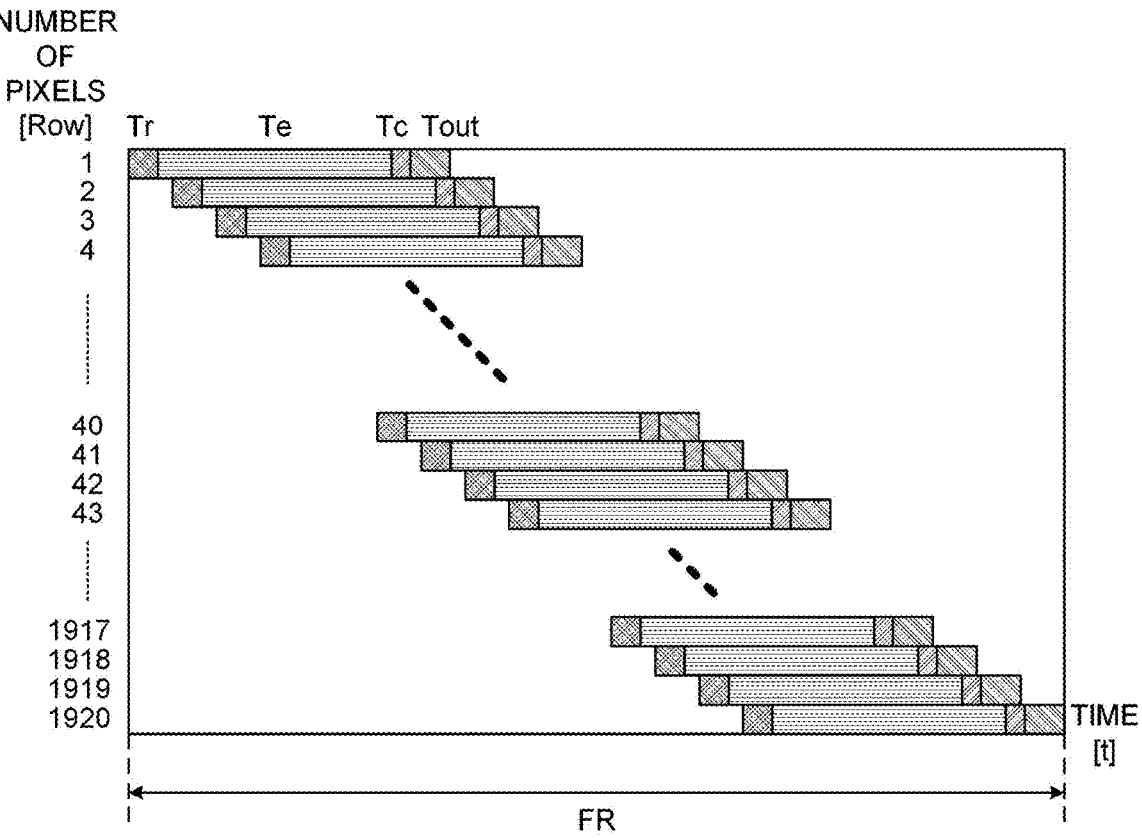
FIG. 7 is an explanatory diagram of the operation of the ophthalmic apparatus according to the embodiments.
Figure 8:
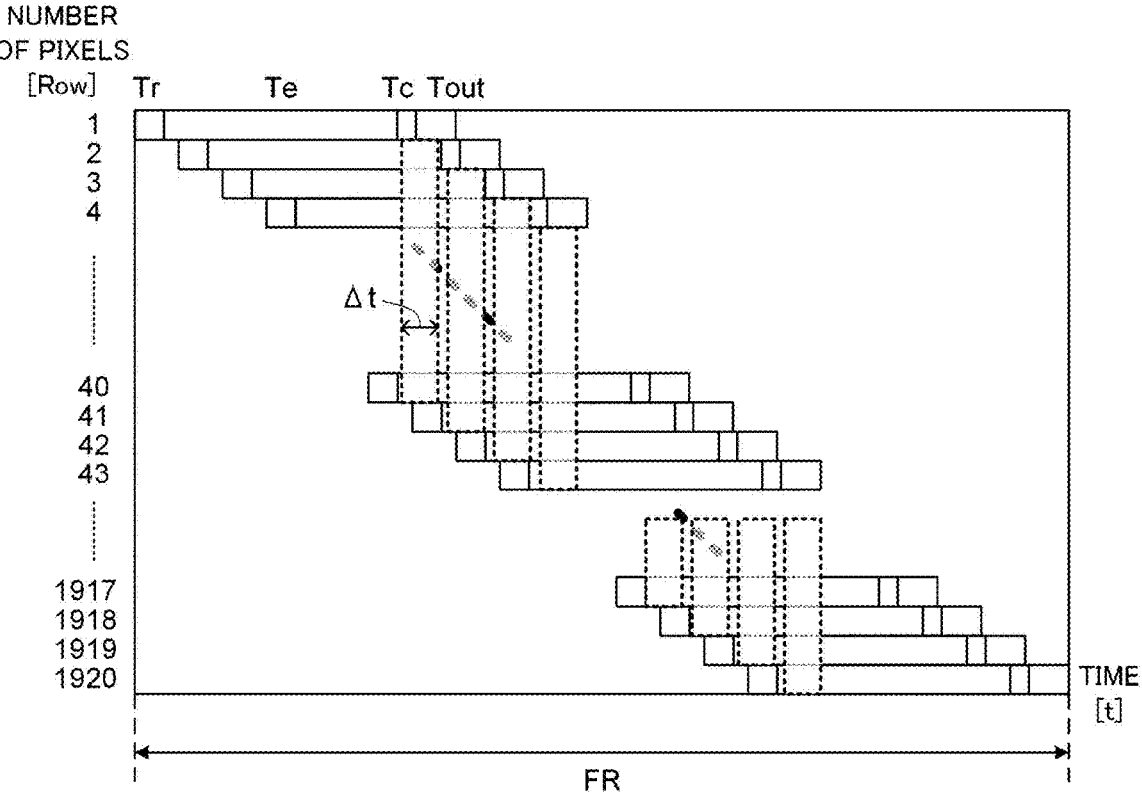
FIG. 8 is an explanatory diagram of the operation of the ophthalmic apparatus according to the embodiments.
Figure 9:
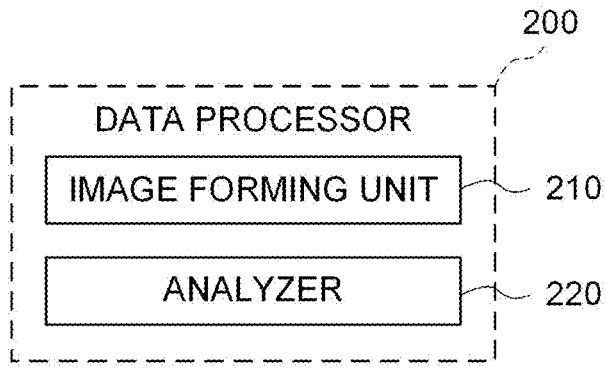
FIG. 9 is a schematic diagram illustrating an example of a configuration of a control system of the ophthalmic apparatus according to the embodiments.
Figure 10:
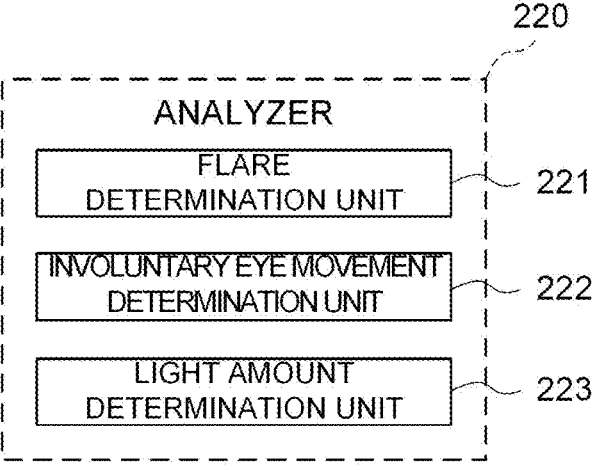
FIG. 10 is a schematic diagram illustrating an example of a configuration of a control system of the ophthalmic apparatus according to the embodiments.

FIGS. 1 to 10 show schematic diagrams of an example of a configuration of an ophthalmic apparatus according to embodiments. FIG. 1 represents an example of a configuration of an optical system of the ophthalmic apparatus 1 according to the embodiments. FIG. 2 representing a block diagram of an example of a configuration of a control system (processing system) of the ophthalmic apparatus 1 according to the embodiments. FIG. 3, FIG. 4A, and FIG. 4B schematically represent examples of the configuration of an iris aperture 21 in FIG. 1 when viewed from a direction of an optical axis O. FIG. 5A and FIG. 5B schematically represent examples of the configuration of an slit 22 in FIG. 1 when viewed from a direction of an optical axis O. FIG. 6 to FIG. 8 show diagrams describing the operation of the ophthalmic apparatus according to the embodiments. FIG. 9 shows a block diagram of an example of the configuration of the data processor 200 of FIG. 2. FIG. 10 represents a block diagram of an example of the configuration of an analyzer 220 in FIG. 9. In FIGS. 1 to 10, like parts are designated by like reference numerals as in repetitious description of such parts may not be provided.

The ophthalmic apparatus 1 includes a first light source 10, a second light source 11, an illumination optical system 20, an optical scanner 30, a projection optical system 35, and an imaging optical system 40, and an imaging device 50. In some embodiments, the illumination optical system 20 includes at least one of the first light source 10, the second light source 11, the optical scanner 30, and the projection optical system 35. In some embodiments, the imaging optical system 40 includes the imaging device 50. In some embodiments, the projection optical system 35 or the imaging optical system 40 includes the optical scanner 30.

In the embodiments, while sharing the optical system (illumination optical system 20, optical scanner 30, projection optical system 35, and imaging optical system 40) including the imaging device 50, an imaging condition for acquiring high quality images of a fundus Ef using slit-shaped light generated from light from the first light source 10 is optimized from an analysis result of a fundus image acquired using light from the second light source 11. In some embodiments, the fundus image is acquired from another apparatus different from the ophthalmic apparatus 1.

(First Light Source 10)

The first light source 10 includes a visible light source that generates light in the visible region. For example, the first light source 10 generates light having a central wavelength in the wavelength range of 420 nm to 700 nm. This type of the first light source 10 includes, for example, an LED (Light Emitting Diode), an LD (Laser Diode), a halogen lamp, or a xenon lamp. In some embodiments, the first light source 10 includes a white light source or a light source capable of outputting light with each color component of RGB. The first light source 10 is arranged at a position non-conjugate optically to the fundus Ef and an iris, respectively.

(Second Light Source 11)

The second light source 11 includes an infrared light source that generates light in the infrared region. For example, the second light source 11 generates light having a central wavelength in the near-infrared wavelength range of 700 nm to 1000 nm. This type of the second light source 11 includes, for example, an LED, an LD, a halogen lamp, or a xenon lamp. In some embodiments, a single light source capable of switching to output light in the visible region and light in the infrared region realizes a function of the first light source 10 and a function of the second light source 11. The second light source 11 is arranged at a position non-conjugate optically to the fundus Ef and the iris, respectively.

A half mirror 12 is arranged between the first light source 10 and the illumination optical system 20. An optical path of the light from the second light source 11 is coaxially coupled with an optical path of the light from the first light source 10 by the half mirror 12. The light from the first light source 10 is transmitted through the half mirror 12, and is guided to the illumination optical system 20. The light from the second light source 11 is reflected by the half mirror 12, and is guided to the illumination optical system 20.

(Illumination Optical System 20)

The illumination optical system 20 generates slit-shaped illumination light using the light from the first light source 10 or the second light source 11. The illumination optical system 20 guides the generated illumination light to the optical scanner 30.

The illumination optical system 20 includes the iris aperture 21, the slit 22, and a relay lens 23. The light from the first light source 10 or the second light source 11 passes through the aperture(s) formed in the iris aperture 21, passes through the aperture formed in the slit 22, and is transmitted through the relay lens 23. The relay lens 23 includes one or more lenses. The light transmitted through the relay lens 23 is guided to the optical scanner 30.

(Iris Aperture 21)

The iris aperture 21 (specifically, aperture(s) described below) can be arranged at a position substantially conjugate optically to the iris (pupil) of a subject's eye E. In the iris aperture 21, one or more apertures are formed at position(s)

away from the optical axis O. For example, as shown in FIG. 3, apertures 21A and 21B having a predetermined thickness along a circumferential direction centered with the optical axis O are formed in the iris aperture 21. The aperture(s) formed in the iris aperture 21 defines an incident position (incident shape) of the illumination light on the iris of the subject's eye E. For example, when the pupil center of the subject's eye E is arranged on the optical axis O, the illumination light can enter into the eye from positions deviated from the pupil center (specifically, point-symmetrical positions centered on the pupil center), by forming the apertures 21A and 21B as shown in FIG. 3.

Further, the light amount distribution of the light passing through the aperture(s) formed in the iris aperture 21 can be changed by changing a relative position between the first light source 10 and the aperture(s) formed in the iris aperture 21.

In the iris aperture 21 according to the embodiments, the size of the opening shape of at least one of the apertures 21A and 21B can be changed.

For example, as shown in FIG. 4A, the iris aperture 21 includes a turret provided orthogonally to the rotation axis O' which is parallel to the optical axis O. The turret is provided so as to be capable of rotating around the rotation axis O'. The turret is provided with a plurality of iris apertures on a circumference centered on the rotation axis O'. By rotating the turret around the rotation axis O', the plurality of iris apertures (iris apertures $21_1$ to $21_3$ in FIG. 4A) can be selectively placed on the optical axis O. The turret can be rotated automatically or manually. For example, a driving mechanism (21D), which receives control from a controller 100 described below, can rotate the turret around the rotation axis O'. In FIG. 4A, the size of the opening shape increases in the order of the iris aperture $21_1$, the iris aperture $21_2$, and the iris aperture $21_3$. In the iris aperture $21_1$, apertures $21A_1$ and $21B_1$ are formed. In the iris aperture $21_2$, apertures $21A_2$ and 21B2 are formed. In the iris aperture $21_3$, apertures $21A_3$ and 21B3 are formed.

Alternatively, as shown in FIG. 4B, for example, the iris aperture 21 includes an optical member $21C_1$ provided substantially orthogonally to the optical axis O and an disk-shaped shielding plate $21C_2$ provided substantially orthogonally to the optical axis O. In the optical member $21C_1$, the apertures 21A and 21B are formed. A length of a radius of the shielding plate $21C_2$ can be changed. A part of the circumference of the shielding plate $21C_2$ constitutes inner diameters of the apertures 21A and 21B. A mechanism not shown in the figure can change the length of the radius of the shielding plate $21C_2$. The length of the radius of the shielding plate $21C_2$ can be automatically or manually changed. For example, the mechanism, which receives control from the controller 100 described below, can change the length of the radius of the shielding plate $21C_2$. By changing the size of the inner diameters of the apertures 21A and 21B in this way, the size of the opening shapes of the apertures 21A and 21B of the iris aperture 21 can be changed.

It should be noted that a case in which the size of the inner diameters of the apertures 21A and 21B are configured to be changed is described in FIG. 4B. However, the size of the outer diameters of the apertures 21A and 21B may be configured to be changed. In this case, by changing the size of the outer diameters of the apertures 21A and 21B, the size of the opening shapes of the apertures 21A and 21B of the iris aperture 21 can be changed.

Thus, by reducing the size of the opening shape of at least one of the apertures 21A and 21B, the light amount of the illumination light passing through the iris aperture 21 can be reduced. By increasing the size of the opening shape of at least one of the apertures 21A and 21B, the light amount of the illumination light passing through the iris aperture 21 can be increased.

In some embodiments, the size of the opening shape of the apertures 21A and 21B of the iris aperture 21 is changed in accordance with a size of a pupil region of the subject's eye E. For example, in the case of the subject's eye E with a large pupil region, the exposure time (imaging time) of the image sensor 51 can be shortened by increasing the size of the opening shape of the apertures 21A and 21B of the iris aperture 21. For example, in the case of the subject's eye E with a small pupil region, the size of the opening shape of the apertures 21A and 21B of the iris aperture 21 can be reduced to compensate for the reduced light amount of the illumination light by changing the imaging condition(s).

In some embodiments, the size of the pupil region is specified by analyzing the anterior segment image of the subject's eye E, and the size of the opening shape of the apertures 21A and 21B of the iris aperture 21 is changed based on the size of the specified pupil region.

(Slit 22)

The slit 22 (specifically, aperture(s) described below) can be arranged at a position substantially conjugate optically to the fundus Ef of the subject's eye E. For example, in the slit 22, the aperture is formed extending in a direction corresponding to a line direction (row direction) that is read out from the image sensor 51 described below using the rolling shutter method. The aperture formed in the slit 22 defines an irradiated pattern of the illumination light on the fundus Ef of the subject's eye E.

The slit 22 can be moved in the optical axis direction of the illumination optical system 20 using a driving mechanism (driving mechanism 22D described below). The driving mechanism moves the slit 22 in the optical axis direction, under the control from the controller 100 described below. For example, the controller 100 controls the driving mechanism in accordance with the state of the subject's eye E. This allows to move the position of the slit 22 in accordance with the state of the subject's eye E (specifically, the dioptric power or the shape of the fundus Ef).

In some embodiments, the slit 22 is configured so that at least one of the position of the aperture and the shape of the aperture can be changed in accordance with the state of the subject's eye E without being moved in the optical axis direction. The function of the slit 22 with this configuration is, for example, realized by a liquid crystal shutter.

In the slit 22 according to the embodiments, the size of the opening shape of the aperture can be changed.

For example, as shown in FIG. 5A, the slit 22 includes a turret provided orthogonally to the rotation axis O" which is parallel to the optical axis O. The turret is provided so as to be capable of rotating around the rotation axis O". The turret is provided with a plurality of slits on a circumference centered on the rotation axis O". By rotating the turret around the rotation axis O", a plurality of slits (slits $22_1$ to $22_3$ in FIG. 5A) can be selectively placed on the optical axis O. The turret can be rotated automatically or manually. For example, the driving mechanism (22D), which receives control from the controller 100 described below, can rotate the turret around the rotation axis O". In FIG. 5A, the size of the opening shape increases in the order of the slit $22_1$, the slit 222, and the slit $22_3$.

Alternatively, as shown in FIG. 5B, for example, the slit 22 includes shielding plates 22A and 22B. The shielding plates 22A and 22B can be slid in a direction substantially orthogonal to the optical axis O. The shielding plates 22A and 22B are slid in opposite directions each other so that the slit width is changed lineally symmetrically with respect to a slit center line passing through the optical axis O. The shielding plates 22A and 22B are slid automatically or manually. For example, the driving mechanism (22D) slides the shielding plates 22A and 22B. For example, the driving mechanism (22D), which receives control from the controller 100 described below, slides the shielding plates 22A and 22B.

Thus, by reducing the width (size of the opening shape) of slit 22, the light mount of the illumination light passing through slit 22 can be reduced. By increasing the width of slit 22, the light amount of the illumination light passing through slit 22 can be increased.

The light from the first light source 10 or the second light source 11 that has passed through the aperture(s) formed in the iris aperture 21 is output as the slit-shaped illumination light by passing through the aperture formed in the slit 22. The slit-shaped illumination light is transmitted through the relay lens 23, and is guided to the optical scanner 30.

(Optical Scanner 30)

The optical scanner 30 is placed at a position substantially conjugate optically to the iris of the subject's eye E. The optical scanner 30 deflects the slit-shaped illumination light transmitted through the relay lens 23 (slit-shaped light passing through the aperture formed in the slit 22). Specifically, the optical scanner 30 deflects the slit-shaped illumination light for sequentially illuminating a predetermined illumination range of the fundus Ef to guide the illumination light to the projection optical system 35, while changing the deflection angle within a predetermined deflection angle range with the iris or the vicinity of the iris of the subject's eye E as a scan center position. The optical scanner 30 can deflect the illumination light one-dimensionally or two-dimensionally.

In case that the optical scanner 30 deflects the illumination light one-dimensionally, the optical scanner 30 includes a galvano scanner that deflects the illumination light within a predetermined deflection angle range with reference to a predetermined deflection direction. In case that the optical scanner 30 deflects the illumination light two-dimensionally, the optical scanner 30 includes a first galvano scanner and a second galvano scanner. The first galvano scanner deflects the illumination light so as to move the irradiated position of the illumination light in a horizontal direction orthogonal to the optical axis of the illumination optical system 20. The second galvano scanner deflects light deflected by the first galvano scanner so as to move the irradiated position of the illumination light in a vertical direction orthogonal to the optical axis of the illumination optical system 20. Examples of scan mode for moving the irradiated position of the illumination light using the optical scanner 30 include a horizontal scan, a vertical scan, a cross scan, a radial scan, a circle scan, a concentric scan, and a helical (spiral) scan.

(Projection Optical System 35)

The projection optical system 35 guides the illumination light deflected by the optical scanner 30 to the fundus Ef of the subject's eye E. In the embodiments, the projection optical system 35 guides the illumination light deflected by the optical scanner 30 through an optical path coupled with an optical path of the imaging optical system 40 by a perforated mirror 45 as the optical path coupling member described below.

The projection optical system 35 includes a relay lens 41, a black point plate 42, a reflective mirror 43, and a relay lens 44. Each of the relay lenses 41 and 44 includes one or more lenses.

(Black Point Plate 42)

The black point plate 42 is arranged at a position substantially conjugate optically to a lens surface of an objective lens 46 or the vicinity of the lens surface of the objective lens 46. This prevents the reflected light from the lens surface of the objective lens 46 from being guided to the imaging device 50.

With such projection optical system 35, the illumination light deflected by the optical scanner 30 is transmitted through the relay lens 41, passes through the black point plate 42, is reflected by the reflective mirror 43 toward the perforated mirror 45.

(Imaging Optical System 40)

The imaging optical system 40 guides the illumination light that has been guided through the projection optical system 35 to the fundus Ef of the subject's eye E, and also guides the returning light of the illumination light from the fundus Ef to the imaging device 50.

In the imaging optical system 40, an optical path of the illumination light from the projection optical system 35 and an optical path of the returning light of the illumination light from the fundus Ef are coupled. By using the perforated mirror 45 as an optical path coupling member to couple these optical paths, it enables pupil division between the illumination light and the returning light of the illumination light.

The imaging optical system 40 includes the perforated mirror 45, the objective lens 46, a focusing lens 47, a relay lens 48, and an imaging lens 49. Each of relay lens 48 includes one or more lenses.

(Perforated Mirror 45)

In the perforated mirror 45, the hole is formed. The hole is arranged on the optical axis of the imaging optical system 40. The hole of the perforated mirror 45 is arranged at a position substantially conjugate optically to the iris of the subject's eye E. The perforated mirror 45 reflects the illumination light from the projection optical system 35 toward the objective lens 46, on the peripheral region of the hole. The perforated mirror 45 with this configuration functions as an imaging aperture (photographic stop).

That is, the perforated mirror 45 is configured to couple the optical path of the illumination optical system 20 (projection optical system 35) and the optical path of the imaging optical system 40 arranged in a direction of the optical axis passing through the hole, and also to guide the illumination light reflected on the peripheral region of the hole to the fundus Ef.

A size of the opening shape of the hole (aperture) in perforated mirror 45 according to the embodiments can be changed using a known mechanism. In some embodiments, the movement mechanism changes the size of the opening shape of the hole in the perforated mirror 45 under the control from the controller 100 described below. In some embodiments, the perforated mirror 45 includes a reflective member with a hole in the central region, and an aperture member disposed inside or near the hole in the reflective member. A known mechanism drives the aperture member to change the size of the opening shape of the hole, under control from the controller 100 described below.

Thus, by reducing the size of the opening shape of the perforated mirror 45, the light amount of the returning light of the illumination light passing through the hole can be reduced. By increasing the size of the opening shape of the perforated mirror 45, the light amount of the returning light of the illumination light passing through the hole can be increased.

(Focusing Lens 47)

The focusing lens 47 can be moved in an optical axis direction of the imaging optical system 40 using a movement mechanism (not shown). The movement mechanism moves the focusing lens 47 in the optical axis direction under the control from the controller 100 described below. This allows to image the returning light of the illumination light passing through the hole of the perforated mirror 45 on the light receiving surface of the image sensor 51 in the imaging device 50 in accordance with the state of the subject's eye E.

In the imaging optical system 40 with this configuration, the illumination light from the projection optical system 35 is reflected toward the objective lens 46 on the peripheral region of the hole formed in the perforated mirror 45. The illumination light reflected on the peripheral region of perforated mirror 45 is refracted by the objective lens 46, enters into the eye through the pupil of the subject's eye E, and illuminates the fundus Ef of the subject's eye E.

The returning light of the illumination light from the fundus Ef is refracted by the objective lens 46, passes through the hole of the perforated mirror 45, is transmitted through the focusing lens 47, is transmitted through the relay lens 48, and is imaged on the light receiving surface of the image sensor 51 in the imaging device 50 through the imaging lens 49.

(Imaging Device 50)

The imaging device 50 includes the image sensor 51 receiving the returning light of the illumination light that has been guided from the fundus Ef of the subject's eye E through the imaging optical system 40. The imaging device 50 can output the light receiving result of the returning light under the control from the controller 100 described below.

(Image Sensor 51)

The image sensor 51 realizes the function as a pixelated photodetector. The light receiving surface (detecting surface, imaging surface) of the image sensor 51 can be arranged at a position substantially conjugate optically to the fundus Ef.

The light receiving result acquired by the image sensor 51 is read out using a rolling shutter method. In some embodiments, the controller 100 described below performs readout control of the light receiving result by controlling the image sensor 51. In some embodiments, the image sensor 51 can automatically output the light receiving results for a predetermined number of lines, along with information indicating the light receiving position(s).

The image sensor 51 with this configuration includes the CMOS image sensor. In this case, the image sensor 51 includes a plurality of pixels (light receiving elements). The plurality of pixels includes a plurality of pixel groups arranged in a column direction. Each of the plurality of pixel groups includes pixels arranged in a row direction. Specifically, the image sensor 51 includes a plurality of pixels arranged two-dimensionally, a plurality of vertical signal lines, and a horizontal signal line. Each pixel includes a photodiode (light receiving element), and a capacitor. The vertical signal lines are provided for each pixel group in the column direction (vertical direction) orthogonal to the row direction (horizontal direction). Each of the vertical signal lines is selectively electrically connected to the pixel group in which the electrical charge corresponding to the light receiving result is accumulated. The horizontal signal line is selectively electrically connected to the vertical signal lines. Each of the pixels accumulates the electrical charge corresponding to the light receiving result of the returning light. The accumulated electrical charge is read out sequentially for each pixel group in the row direction, for example. For example, for each line in the row direction, a voltage corresponding to the electrical charge accumulated in each pixel is supplied to the vertical signal line. The vertical signal lines are selectively electrically connected to the horizontal signal line. By performing readout operation for each line in the row direction described above sequentially in the vertical direction, the light receiving results of the plurality of pixels arranged two-dimensionally can be read out.

By capturing (reading out) the light receiving results of the returning light using the rolling shutter method for this type of image sensor 51, the light receiving image corresponding to the desired virtual opening shape extending in the row direction is acquired. Such control is disclosed in, for example, U.S. Pat. No. 8,237,835.

FIG. 6 shows a diagram explaining the operation of the ophthalmic apparatus 1 according to the embodiments. FIG. 6 schematically represents an irradiated range IP of the slit-shaped illumination light irradiated on the fundus Ef and a virtual opening range OP on the light receiving surface SR of the image sensor 51.

For example, the controller 100 described below deflects the slit-shaped illumination light formed by the illumination optical system 20, using the optical scanner 30. Thereby, the irradiated range IP of the slit-shaped illumination light is sequentially moved (shifted) in a direction (for example, the vertical direction) orthogonal to the slit direction (for example, the row direction, the horizontal direction) on the fundus Ef.

On the light receiving surface SR of the image sensor 51, for example, by changing the pixels to be captured in units of lines by the controller 100 described below, the virtual opening range (opening region) OP is set. The opening range OP is preferable to be the light receiving range IP' of the returning light of the illumination light on the light receiving surface SR or wider than the light receiving range IP'. For example, the controller 100 described below performs the movement control of the opening range OP in synchronization with the movement control of the irradiated range IP of the illumination light. Thereby, without being affected by unnecessary scattered light, high quality images of the fundus Ef with strong contrast can be acquired using a simple configuration.

FIGS. 7 and 8 schematically show examples of the control timing of the rolling shutter method for the image sensor 51. FIG. 7 represents an example of the timing of the readout control for the image sensor 51. FIG. 8 represents the timing of the movement control for the irradiated range IP (the light receiving range IP') superimposed on the timing of the readout control in FIG. 7. In FIGS. 7 and 8, the horizontal axis represents the number of rows in the image sensor 51, and the vertical axis represents time.

In addition, in FIGS. 7 and 8, for convenience of explanation, it is assumed that the number of rows in the image sensor 51 is 1920. However, the configuration according to the embodiments is not limited to the number of rows. Further, in FIG. 8, for convenience of explanation, it is assumed that the slit width (width in the row direction) of the slit-shaped illumination light is 40 rows.

The readout control in the row direction includes the reset control, the exposure control, the charge transfer control, and the output control. The reset control is a control that initializes the amount of electrical charge accumulated in the pixels in the row direction. The exposure control is a control that illuminates light on the photodiode and accumulates the electrical charge corresponding to the amount of received light in the capacitor. The charge transfer control is a control that transfers the amount of the electrical charge accumulated in the pixel to the vertical signal line. The output control is a control that outputs the amount of the electrical charge accumulated in the plurality of vertical signal lines via the horizontal signal line. That is, as shown in FIG. 7, the readout time T for reading out the electrical charge accumulated in the pixels in the row direction is the sum of the time Tr required for the reset control, the time Te required for the exposure control (exposure time), the time Tc required for the charge transfer control, and the time Tout required for the output control.

In FIG. 7, by shifting the readout (capturing) start timing (start timing of time Tc) in units of rows, the light receiving results (amount of electrical charge) accumulated in the pixels in the desired range in the image sensor 51 are acquired. For example, in case that the pixel range shown in FIG. 7 is for a single frame of the image, the frame rate FR is determined uniquely.

In this embodiment, the irradiated position of the illumination light on the fundus Ef, the illumination light having a slit width for a plurality of rows, is sequentially shifted in a direction corresponding to the column direction on the fundus Ef. When the width in the shift direction of the irradiated range IP' (a region corresponding to the illumination region on the fundus Ef) on the light receiving surface of the image sensor 51 has two or more rows, the controller 100 described below controls the optical scanner 30 so that the opening range OP (opening region) shifts in the shift direction in units of a predetermined number of rows.

For example, as shown in FIG. 8, at each predetermined shift time $\Delta t$, the irradiated position of the illumination light on the fundus Ef is shifted in row units in the direction corresponding to the column direction. The shift time $\Delta t$ is obtained by dividing the exposure time Te of the pixel in the image sensor 51 by the slit width (e.g., the number of rows of the slit width=40) of the illumination light ($\Delta t$=Te/40). Synchronized with this movement timing of this irradiated position, the readout start timing of each row of pixels is delayed and is started for each row in units of shift time $\Delta t$. This allows to acquired high quality images of the fundus Ef with strong contrast in a short time with a simple control.

In some embodiments, the image sensor 51 is configured using one or more line sensors.

[Configuration of Control System]

As shown in FIG. 2, the control system of the ophthalmic apparatus 1 is configured with a controller 100 as a center. It should be noted that at least a part of the configuration of the control system may be included in the ophthalmic apparatus 1.

(Controller 100)

The controller 100 controls each part of the ophthalmic apparatus 1. The controller 100 includes a main controller 101 and a storage unit 102. The main controller 101 includes a processor and executes the control processing of each part of the ophthalmic apparatus 1 by executing processing according to the program(s) stored in the storage unit 102.

(Main Controller 101)

The main controller 101 performs control for the first light source 10, control for the second light source 11, control for the movement mechanism 10D, control for the illumination optical system 20, control for the optical scanner 30, control for the imaging optical system 40, control for the imaging device 50, and control for the data processor 200.

The control for the first light source 10 includes switching the light source on and off (or switching the wavelength region of the light), and changing the light amount of the light source.

The control for the second light source 11 includes switching the light source on and off (or switching the wavelength region of the light), and changing the light amount of the light source.

When the function of the first light source 10 and the function of the second light source 11 are realized by a single light source, the main controller 101 can perform switching control between the function of the first light source 10 and the function of the second light source 11.

The movement mechanism 10D changes at least one of the position of the first light source 10 and the orientation of the first light source 10 using a known mechanism. The main controller 101 can change at least one of a relative position of the first light source 10 to the iris aperture 21 and the slit 22, or a relative orientation of the first light source 10 to the iris aperture 21 and the slit 22.

The control for the illumination optical system 20 includes control for the driving mechanisms 21D and 22D. The driving mechanism 21D changes the size of the opening shape of at least one of the apertures 21A and 21B on the iris aperture 21. The main controller 101 can control the driving mechanism 21D to change the size of the opening shape of at least one of the apertures 21A and 21B of the iris aperture 21.

The driving mechanism 22D moves the slit 22 in the optical axis direction of the illumination optical system 20 or changes the slit width of the slit 22.

The main controller 101 controls the driving mechanism 22D in accordance with the state of the subject's eye E to arrange the slit 22 at the position corresponding to the state of the subject's eye E. Examples of the state of the subject's eye E includes a shape of the fundus Ef, a dioptric power, and an axial length. The dioptric power can be obtained from a known eye refractive power measurement apparatus as disclosed in Japanese Unexamined Patent Application No. 61-293430 or Japanese Unexamined Patent Application Publication No. 2010-259495, for example. The axial length can be obtained from a known axial length measurement apparatus or a measurement value acquired by an optical coherence tomography.

For example, the storage unit 102 stores first control information. In the first control information, the positions of the slit 22 on the optical axis of the illumination optical system 20 are associated with the dioptric powers in advance. The main controller 101 specifies the position of the slit 22 corresponding to the dioptric power by referring to the first control information, and controls the driving mechanism 22D so as to arrange the slit 22 at the specified position.

Here, as the slit 22 moves, the light amount distribution of the light passing through the aperture formed in the slit 22 changes. In this case, as described above, the main controller 101 can control the movement mechanism 10D to change at least one of the position of the first source 10 and the orientation of the first light source 10.

Further, the main controller 101 can control the driving mechanism 22D to change the size of the slit width of the slit 22.

The control for the optical scanner 30 includes control of the angle of the deflection surface deflecting the illumination light. By controlling an angle range of the deflection surface, the scan range (scan start position and scan end position) can be controlled. By controlling a change speed of the angle of the deflection surface, the scan speed can be controlled.

The control for the imaging optical system 40 includes a control for a movement mechanism 47D. The movement mechanism 47D moves the focusing lens 47 in the optical axis direction of the imaging optical system 40. The main controller 101 can control the movement mechanism 47D based on an analysis result of the image acquired using the image sensor 51. Further, the main controller 101 can control the movement mechanism 47D based on a content of operation of the user using an operation unit 110 described below.

The control for the imaging device 50 includes a control for the image sensor 51. The control for the image sensor 51 includes a control for reading out the light receiving result using a rolling shutter method (for example, setting of light receiving size corresponding to the size of the illumination pattern, or the like). Further, the control for the image sensor 51 includes the reset control, the exposure control, the charge transfer control, and the output control. The time Tr required for the reset control, the time (exposure time) Te required for the exposure control, the time Tc required for the charge transfer control, and the time Tout required for the output control, etc., can be changed.

Examples of the control for the data processor 200 include various kinds of image processing and various kinds of analysis processing on the light receiving results acquired from the image sensor 51. Examples of the image processing include noise removal processing on the light receiving results, brightness correction processing for easily identifying a predetermined site depicted in the light receiving image based on the light receiving results. Examples of the analysis processing include a specifying processing of the in-focus state.

(Data Processor 200)

The data processor 200 includes an image forming unit 210 and an analyzer 220, as shown in FIG. 9.

(Image Forming Unit 210)

The image forming unit 210 can form the light receiving image corresponding to the arbitrary opening range based on the light receiving result(s) read out from the image sensor 51 using the rolling shutter method. The image forming unit 210 can sequentially form light receiving light images corresponding to the opening ranges and form an image of the subject's eye E from a plurality of formed light receiving images.

The image forming unit 210 can form an image (captured image) of the fundus Ef based on the light receiving result(s) of the returning light. Here, the light receiving result(s) can be captured by the image sensor 51 using the rolling shutter method, by irradiating the illumination light generated using the light from the first light source 10 onto the fundus Ef. Further, the image forming unit 210 can form the fundus image (IR image) based on the light receiving result(s). Here, the light receiving result(s) can be captured by the image sensor 51 using the rolling shutter method, by irradiating the illumination light generated using the light from the second light source 11 onto the fundus Ef.

(Analyzer 220)

The analyzer 220 performs predetermined analysis processing on the fundus image formed by the image forming unit 210, for example. Examples of the predetermined analysis processing include a determination processing for changing the imaging condition(s). Specifically, the analyzer 220 performs the determination processing for changing the imaging condition(s) so as to acquire higher quality captured images.

As shown in FIG. 10, such analyzer 220 includes a flare determination unit 221, an involuntary eye movement determination unit 222, and a light amount determination unit 223.

(Flare Determination Unit 221)

The flare determination unit 221 analyzes the image to determine whether or not flare occurs. Specifically, the flare determination unit 221 determines whether or not the flare occurs, by analyzing the fundus image (IR image) formed based on the light receiving result(s) captured by the image sensor 51 using the light from the second light source 11.

In some embodiments, the flare determination unit 221 specifies a region of pixels having a luminance level equal to or higher than a predetermined luminance level based on the luminance components of pixels in the fundus image, determines that the flare occurs when the size of the specified region is equal to or greater than a predetermined size, and determines that the flare does not occur when the size of the specified region is less than the predetermined size. In some embodiments, the flare determination unit 221 determines that the flare occurs when it is determined that the shape of the specified region substantially matches a predetermined shape, and determines that the flare does not occur when it is determined that the shape of the specified region does not substantially match the predetermined shape.

(Involuntary Eye Movement Determination Unit 222)

The involuntary eye movement determination unit 222 analyzes the image to determine whether or not the involuntary eye movement is large (small). Specifically, the involuntary eye movement determination unit 222 determines whether or not the involuntary eye movement is large (small) by analyzing the fundus image (IR image) formed based on the light receiving result(s) captured by the image sensor 51 using the light from the second light source 11.

In some embodiments, the involuntary eye movement determination unit 222 specifies a characteristic region in the fundus image, and determines, based on a displacement of the specified characteristic region, whether or not the involuntary eye movement is large. For example, the involuntary eye movement determination unit 222 determines that the involuntary eye movement is large when the displacement of the characteristic region is equal to or greater than a predetermined movement amount, and determines that the involuntary eye movement is small when the displacement of the characteristic region is less than the predetermined movement amount. Examples of the characteristic region include an optic disc, a fovea, a blood vessel, and a lesion in the fundus.

(Light Amount Determination Unit 223)

The light amount determination unit 223 determines whether or not the light amount of the light output from the first light source 10 can be increased. The light amount determination unit 223 determines whether or not the light amount of the light output from the first light source 10 can be increased, by determining whether or not there is a margin in the light source capability, based on a predetermined maximum value of the output light amount of the first light source 10 and a current output light amount of the first light source 10. For example, when it is determined that there is a margin in the light source capability of the first light source 10, the light amount determination unit 223 determines that the light amount of the light output from the first light source 10 can be increased. For example, when it is determined that there is not a margin in the light source capability of the first light source 10, the light amount determination unit 223 determines that the light amount of the light output from the first light source 10 cannot be increased.

The data processor 200 includes a processor, and realizes the above functions by performing processing corresponding to the program(s) stored in the storage unit or the like.

In some embodiments, the data processor 200 includes a processor corresponding to each of the parts of the data processor 200, and each processor realizes a function of each parts of the data processor 200.

In some embodiments, the first light source 10 includes two or more light sources. In this case, each of the two or more light sources is provided corresponding to the two or more apertures formed in the iris aperture 21 or the two or more apertures formed in the slit 22. The main controller 101 can change the at least one of a position of each light source and an orientation (orientation in the direction of maximum light amount distribution) of each light source, by controlling the movement mechanisms provided for each of the two or more light sources.

(Storage Unit 102)

The storage unit 102 stores various computer programs and data. The computer programs include an arithmetic program and a control program for controlling the ophthalmic apparatus 1.

(Operation Unit 110)

The operation unit 110 includes an operation device or an input device. The operation unit 110 includes buttons and switches (e.g., operation handle, operation knob, etc.) and operation devices (e.g., mouse, keyboard, etc.) provided in the ophthalmic apparatus 1. In addition, the operation unit 110 may include any operation device or any input device, such as a trackball, a control panel, a switch, a button, a dial, etc.

(Display Unit 120)

The display unit 120 displays the image of the subject's eye E generated by data processor 200. The display unit 120 is configured to include a display device such as a flat panel display such as an LCD (Liquid Crystal Display). In addition, the display unit 120 may include various types of display devices such as a touch panel and the like provided in the housing of the ophthalmic apparatus 1.

It should be noted that the operation unit 110 and the display unit 120 do not need to be configured to be separate devices. For example, a device like a touch panel, which has a display function integrated with an operation function, can be used. In this case, the operation unit 110 includes the touch panel and a computer program. The content for the operation unit 110 is fed to the controller 100 as electrical signals. Moreover, operations and inputs of information may be performed using a graphical user interface (GUI) displayed on the display unit 120 and the operation unit 110. In some embodiments, the functions of the display unit 120 and the operation unit 110 are realized a touch screen.

(Other Configurations)

In some embodiments, the ophthalmic apparatus 1 further includes a fixation projection system. For example, an optical path of the fixation projection system is coupled with the optical path of the imaging optical system 40 in the configuration of the optical system shown in FIG. 1. The fixation projection system can present internal fixation targets or external fixation targets to the subject's eye E. In case of presenting the internal fixation target to the subject's eye E, the fixation projection system includes an LCD that displays the internal fixation target under the control from the controller 100, and projects a fixation light flux output from the LCD onto the fundus Ef of the subject's eye E. The LCD is configured to be capable of changing the display position of the fixation target on the screen of the LCD. By changing the display position of the fixation target on the screen of the LCD, the projected position of the fixation target on the fundus of the subject's eye E can be changed. The display position of the fixation target on the LCD can be designated using the operation unit 110 by the user. In some embodiments, the fixation projection system is provided with an OLED instead of an LCD.

In some embodiments, the ophthalmic apparatus 1 includes an alignment system. In some embodiments, the alignment system includes an XY alignment system and a Z alignment system. The XY alignment system is used for position matching between the optical system of the apparatus and the subject's eye E in a direction intersecting the optical axis of the optical system of the apparatus (objective lens 46). The Z alignment system is used for position matching between the optical system of the apparatus and the subject's eye E in a direction of the optical axis of the ophthalmic apparatus 1 (objective lens 46).

For example, the XY alignment system projects a bright spot (bright spot in the infrared region or near-infrared region) onto subject's eye E. The data processor 200 acquires an anterior segment image of the subject's eye E on which the bright spot is projected, and obtains the displacement between the bright spot image drawn on the acquired anterior segment image and an alignment reference position. The controller 100 relatively moves the optical system of the apparatus and the subject's eye E in the direction intersecting the direction of the optical axis so as to cancel the obtained displacement, using the movement mechanism.

For example, the Z alignment system projects alignment light in infrared region or the near-infrared region from a position away from the optical axis of the optical system of the apparatus, and receives the alignment light reflected on the anterior segment of the subject's eye E. The data processor 200 specifies a distance to the subject's eye E with respect to the optical system of the apparatus, from the light receiving position of the alignment light that changes in accordance with the distance to the subject's eye E with respect to the optical system of the apparatus. The controller 100 relatively moves the optical system of the apparatus and the subject's eye E in the direction of the optical axis using the movement mechanism (not shown) so that the specified distance becomes a predetermined working distance.

In some embodiments, the function of the alignment system is realized by two or more anterior segment cameras arranged at positions away from the optical axis of the optical system of the apparatus. For example, as disclosed in Japanese Unexamined Patent Application Publication No. 2013-248376, the data processor 200 analyzes data processor segment images of subject's eye E substantially simultaneously acquired using the two or more anterior segment cameras, and specifies a three-dimensional position of the subject's eye E using known trigonometry. The controller 100 controls the movement mechanism (not shown) to relatively move the optical system of the apparatus and the subject's eye E three-dimensionally so that the optical axis of the optical system of the apparatus substantially coincides with an axis of the subject's eye E and the distance of the optical system of the apparatus with respect to the subject's eye E is a predetermined working distance.

As described above, in the ophthalmic apparatus 1, the slit 22 (aperture), an imaging site (fundus Ef), and the image sensor 51 (light receiving surface) are arranged at positions substantially conjugate optically each other. The ophthalmic apparatus 1 can acquire a clear image of the imaging site while suppressing the effects due to the unnecessary scattered light, by moving the light receiving opening on the image sensor 51 in conjunction with the irradiated position of the illumination light.

The perforated mirror 45 is an example of the "imaging aperture" according to the embodiments. The second light source 11, the half mirror 12, the illumination optical system 20, the optical scanner 30, the projection optical system 35, the imaging optical system 40, the imaging device 50, the controller 100, and the image forming unit 210 are an example of the "acquisition unit" according to the embodiments. The apertures 21A and 21B formed in the iris aperture 21 are an example of the "second aperture" according to the embodiments. The aperture formed in the slit 22 is an example of the "first aperture" according to the embodiments. The hole formed in the perforated mirror 45 is an example of the "third aperture" according to the embodiments.

[Operation]

Next, the operation of the ophthalmic apparatus 1 will be described.

Figure 11:
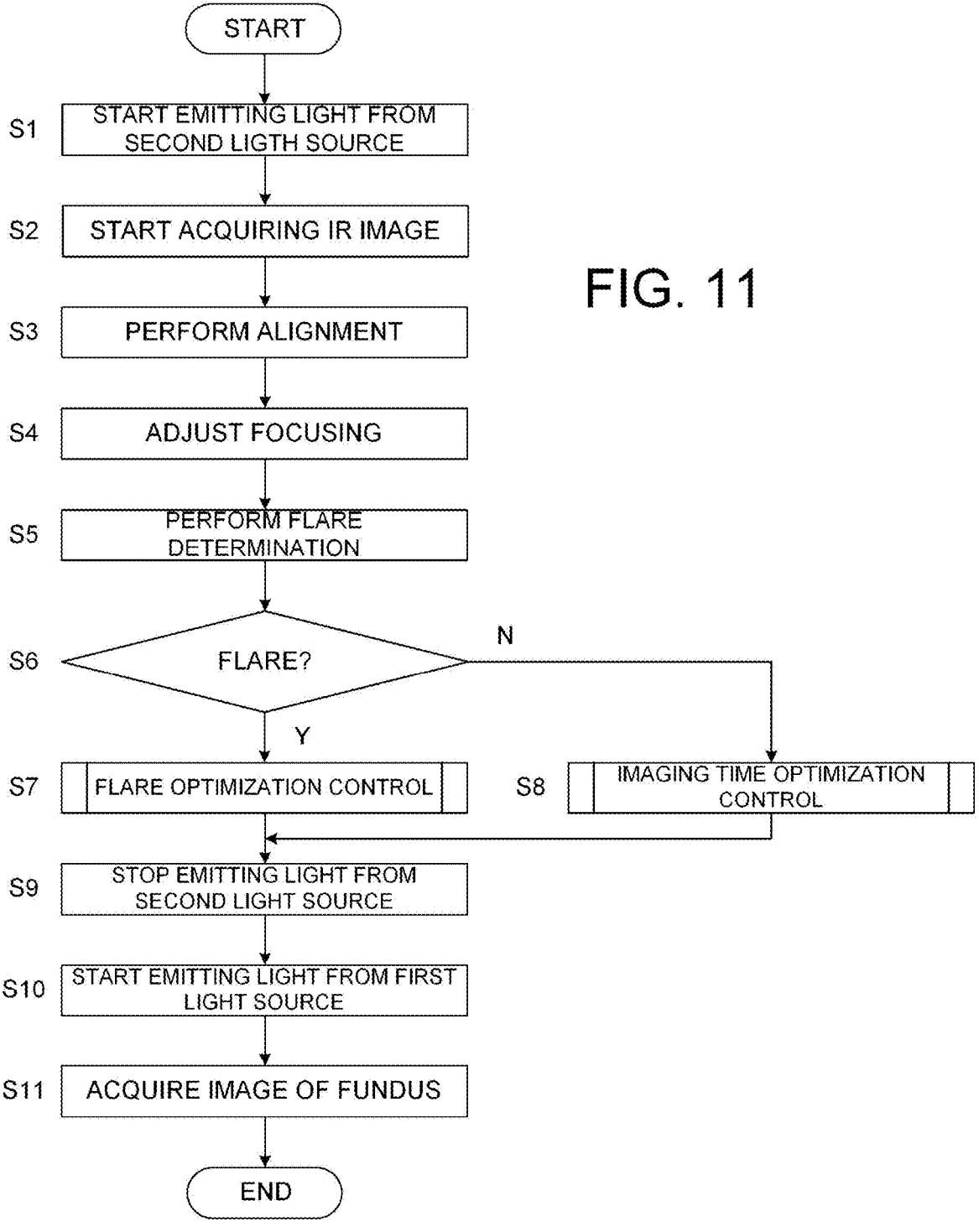
FIG. 11 is a schematic diagram illustrating a flow of an operation example of the ophthalmic apparatus according to the embodiments.
Figure 12:
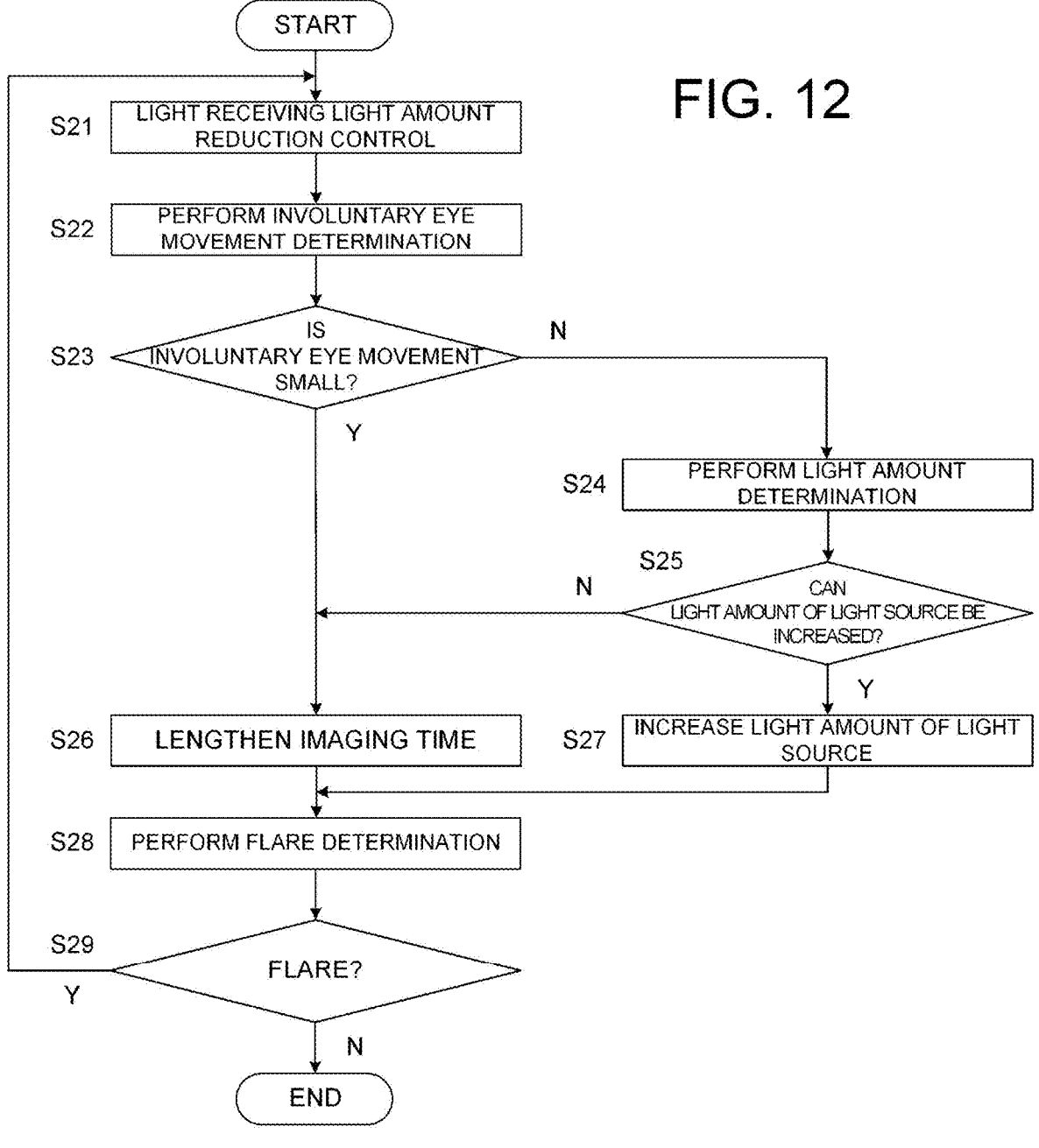
FIG. 12 is a schematic diagram illustrating a flow of an operation example of the ophthalmic apparatus according to the embodiments.
Figure 13:
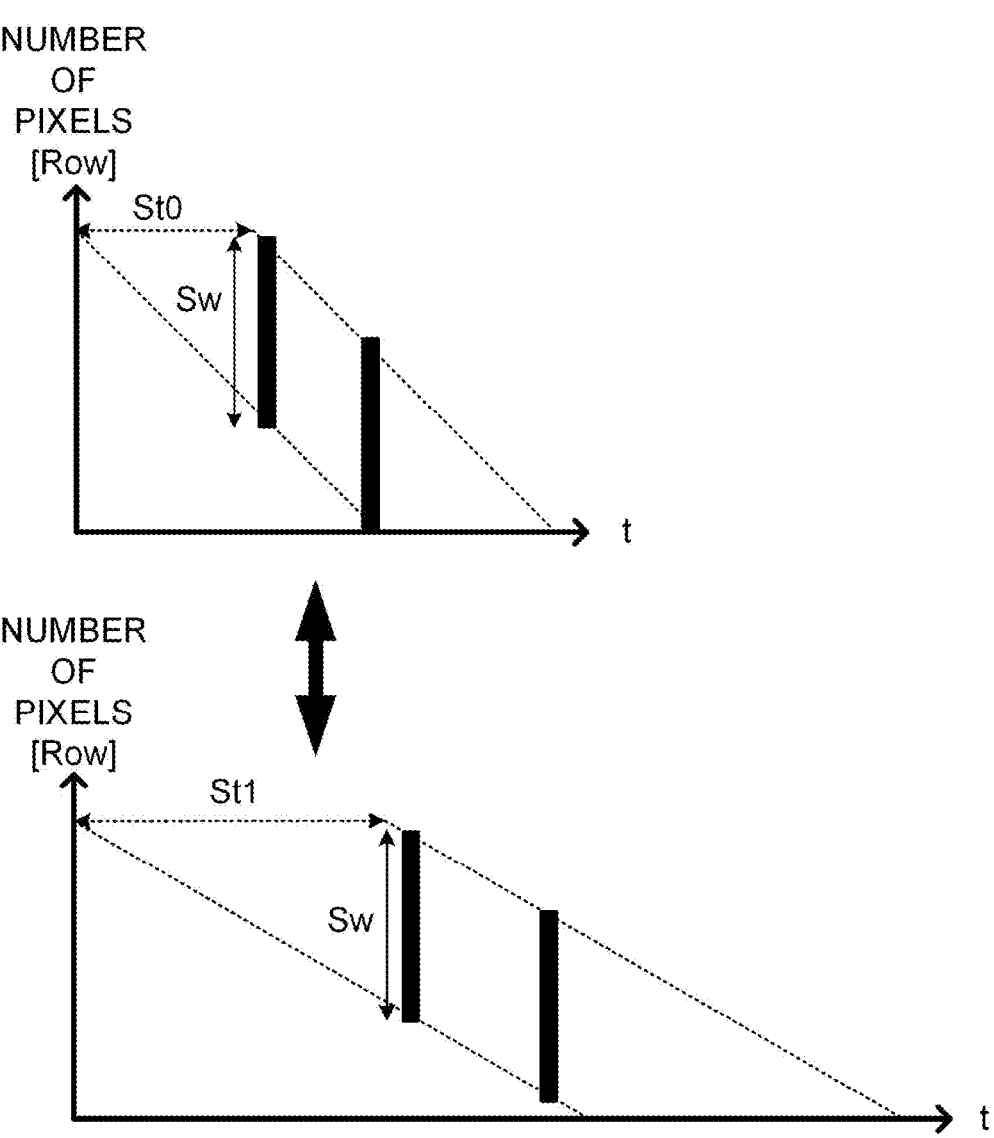
FIG. 13 is an explanatory diagram of the operation of the ophthalmic apparatus according to the embodiments.
Figure 14:
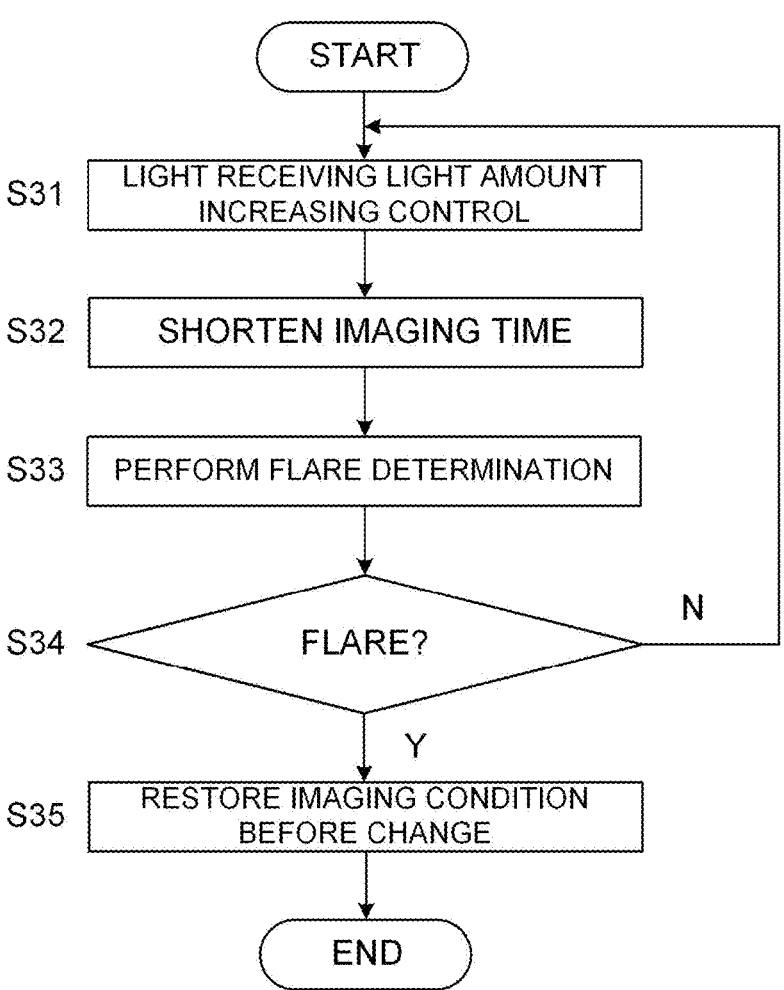
FIG. 14 is a schematic diagram illustrating a flow of an operation example of the ophthalmic apparatus according to the embodiments.
Figure 15:
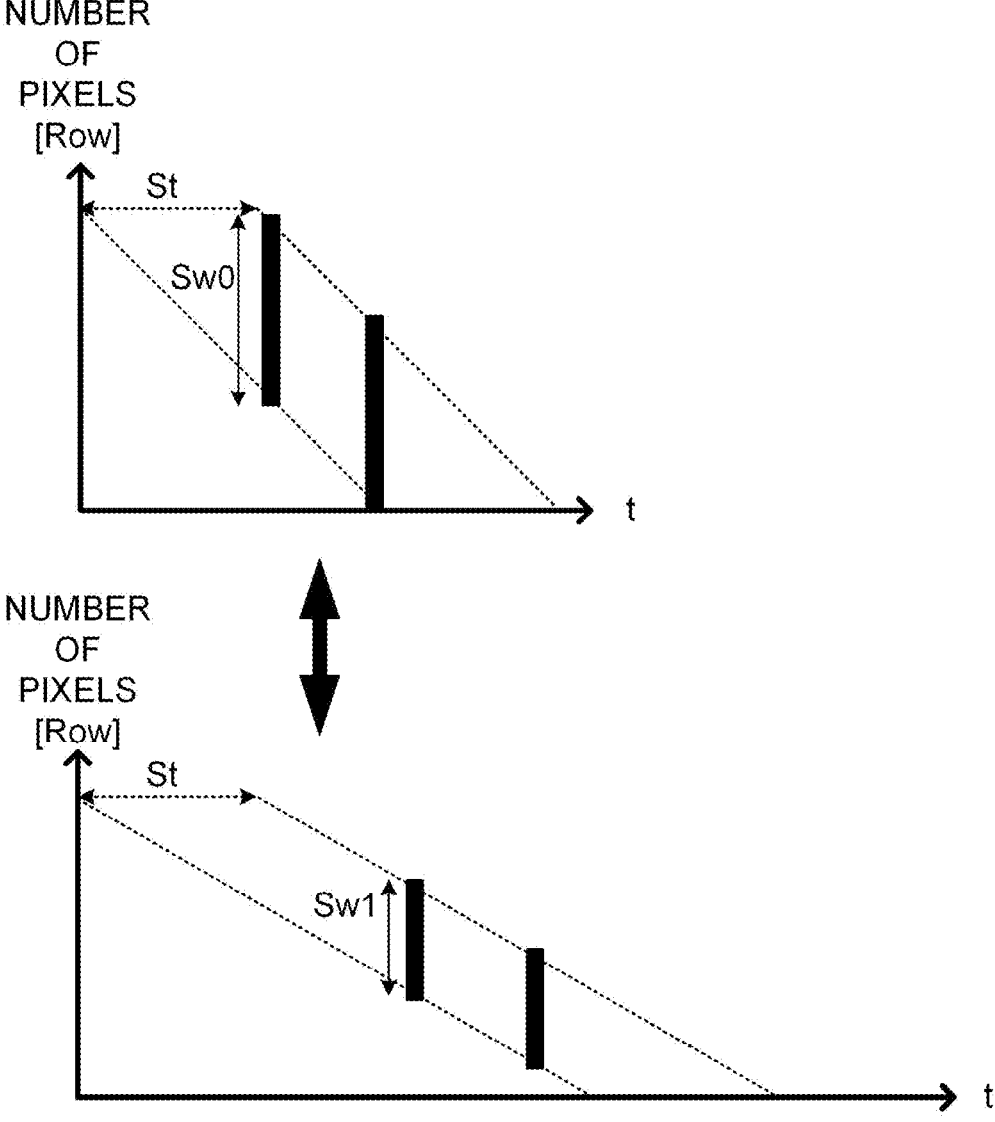
FIG. 15 is an explanatory diagram of the operation of the ophthalmic apparatus according to the embodiments.

FIG. 11, FIG. 12, and FIG. 14 show flowcharts of examples of the operation of the ophthalmic apparatus 1 according to the embodiments. FIG. 13 and FIG. 15 show diagrams describing the operation of the ophthalmic apparatus 1 according to the embodiments. FIG. 11, FIG. 12, and FIG. 14 represent flowcharts of the example of the operation of the ophthalmic apparatus 1 according to the embodiments. FIG. 12 shows a flowchart of an example of the operation of step S7 in FIG. 11. FIG. 14 shows a flowchart of an example of the operation of step S8 in FIG. 11. FIG. 13 represents a diagram describing an example of the operation in FIG. 12. FIG. 15 represents a diagram describing an example of the operation in FIG. 14. The storage unit 102 stores computer programs for realizing the processing shown in FIG. 11, FIG. 12, and FIG. 14. The main controller 101 operates according to the computer programs, and thereby the main controller 101 performs the processing shown in FIG. 11, FIG. 12, and FIG. 14.

(S1: Start Emitting Light from Second Light Source)

First, the ophthalmic apparatus 1 acquires the IR image using the second light source 11, in order to optimize the imaging condition(s) for acquiring high quality captured images using the first light source 10.

Specifically, the main controller 101 controls the second light source 11 so as to start emitting light of the second light source 11. In this case, the main controller 101 may control the fixation projection system not shown to project a fixation target onto a predetermined fixation position on the fundus Ef by performing a predetermined operation on the operation unit 110 by the examiner, in a state where the face of the subject is fixed on a face supporter (not shown).

(S2: Start Acquiring IR Image)

Subsequently, the main controller 101 controls the optical scanner 30, the imaging device 50, and the image forming unit 210 to start acquiring IR images. In this case, the main controller 101 can control the optical scanner 30 to scan an imaging region for acquiring IR images with the illumination light. In some embodiments, the main controller 101 controls the optical scanner 30 to scan the same region as the imaging region for acquiring the captured image described below with the illumination light.

(S3: Perform Alignment)

Next, the main controller 101 performs alignment (XY alignment, Z alignment).

For example, the main controller 101 controls the alignment system not shown to project the bright spot onto the subject's eye E. The main controller 101 specifies an bright spot image in the IR image acquired using the image sensor 51, and controls a movement mechanism not shown based on a movement amount of the optical system corresponding to a displacement of the bright spot image with reference to a predetermined alignment reference position (reference range) to relatively move the optical system to the subject's eye E by the movement amount. The main controller 101 repeatedly performs this processing.

In some embodiments, the alignment is performed manually. For example, the main controller 101 displays a composite image in which an image representing the predetermined alignment reference position (reference range) is superimposed on the IR image on the display unit 120. A user such as the examiner performs operation(s) on the operation unit 110 while viewing the composite image displayed on the display unit 120. The user performs operations on the operation unit 110 so as to cancel a displacement of a desired site in the image relative to the predetermined alignment reference position. The main controller 101 controls a movement mechanism not shown based on operation signal(s) corresponding to the operation content for the operation unit 110.

(S4: Adjust Focusing)

Subsequently, the main controller 101 performs adjustment of focusing.

In some embodiments, the processing in step S4 is performed automatically, after the alignment in step S3 is completed. For example, when the displacement of the desired site relative to the alignment reference position becomes equal to or less than a predetermined threshold, the main controller 101 judges that the alignment in step S3 is complete and performs the processing in step S4.

In some embodiments, when the user performs a predetermined operation on the operation unit 110 in step S3, the main controller 101 performs the processing in step S4.

For example, the main controller 101 acquires the IR image of the fundus Ef and controls the data processor 200 to determine the focus state of the acquired IR image. The data processor 200 can determine the focus state of the IR image using a known method. For example, the data processor 200 determines the focus state of the IR image based on a gradient of the luminance component in the edge region that demarcates the predetermined site in the characteristic region in the IR image. The main controller 101 specifies the movement amount in the optical axis direction of the focusing lens 47 based on the determination result of the focus state obtained by the data processor 200, and controls the movement mechanism 47D based on the specified movement amount. When it is judged that the focus state of the IR image is not appropriate based on the determination result obtained by the data processor 200, the main controller 101 controls the movement mechanism 47D again and repeats this until it is judged that the focus state is appropriate.

In some embodiments, the focus adjustment is performed manually. For example, the main controller 101 displays the IR image on the display unit 120. The user performs operations on the operation unit 110 while viewing the IR image displayed on the display unit 120. The user performs operations on the operation unit 110 so that the focus state of the IR image is appropriate. The main controller 101 controls the movement mechanism 47D based on operation signal(s) corresponding to the operation content for the operation unit 110.

(S5: Perform Flare Determination)

Subsequently, the main controller 101 controls the flare determination unit 221 to perform flare determination.

In some embodiments, the processing in step S5 is performed automatically, after the focus adjustment in step S4 is completed. For example, when it is determined that the focus state is appropriate, the main controller 101 judges that the focus adjustment in step S4 is complete and performs the processing in step S5.

In some embodiments, when the user performs a predetermined operation on the operation unit 110 in step S4, the main controller 101 performs the processing in step S5.

The flare determination unit 221 determines whether or not the flare occurs, by analyzing the IR image, as described above.

(S6: Flare?)

The main controller 101 judges, based on the determination result obtained by performing the flare determination processing in step S5, whether or not the flare occurs in the IR image.

When it is judged in step S6 that the flare occurs in the IR image (S6: Y), the processing of the ophthalmic apparatus 1 proceeds to step S7. On the other hand, when it is judged that the flare does not occur in the IR image (S6: N), the processing of the ophthalmic apparatus 1 proceeds to step S8.

(S7: Flare Optimization Control)

When it is judged in step S6 that the flare occurs in the IR image (S6: Y), the main controller 101 performs flare optimization control. In the flare optimization control, the imaging condition of the fundus Ef is optimized so that the flare does not occur in the IR image (captured image) of the fundus Ef. The details of step S7 will be described below.

Subsequent to step S7, the processing in step S9 is performed.

(S8: Imaging Time Optimization Control)

When it is judged in step S6 that the flare does not occur in the IR image (S6: N), the main controller 101 performs imaging time optimization control. In the imaging time optimization control, the imaging condition of the fundus Ef is optimized so that the imaging time using the image sensor 51 is shortened to the extent that the flare does not occur in the IR image (captured image) of the fundus Ef. The details of step S8 will be described below.

Subsequent to step S8, the processing in step S9 is performed.

(S9: Stop Emitting Light from Second Light Source)

Subsequent to step S7 or step S8, the main controller 101 perform processing in step S9. In step S9, the main controller 101 controls the second light source 11 to stop emitting light of the second light source 11. Thereby, the acquisition of IR images that has been started in step S2 is stopped.

(S10: Start Emitting Light from First Light Source)

Subsequently, the ophthalmic apparatus 1 starts acquiring captured images of the fundus Ef under the imaging condition optimized in step S7 or step S8.

Specifically, the main controller 101 controls the first light source 10 so as to start emitting light of the first light source 10.

(S11: Acquire Image of Fundus)

Subsequently, the main controller 101 controls the optical scanner 30, the imaging device 50, and the image forming unit 210 to start acquiring captured images of the fundus Ef using the first light source 10. In this case, the main controller 101 controls the optical scanner 30 so as to scan a predetermined imaging region on the fundus Ef with the illumination light, and controls the image forming unit 210 to form the captured images of the fundus Ef.

This terminates the operation of the ophthalmic apparatus 1 (END).

In step S7 in FIG. 11, the processing as shown in FIG. 12 is performed.

(S21: Light Receiving Light Amount Reduction Control)

First, the main controller 101 controls at least one of the illumination optical system 20 and the imaging optical system 40 so that the light receiving light amount of the returning light of the illumination light on the image sensor 51 is reduced.

The control for the illumination optical system 20 includes control for the iris aperture 21, and control for the slit 22. The control for the imaging optical system 40 includes control for the perforated mirror 45.

In the first example of the light receiving light amount reduction control, the main controller 101 performs control for the iris aperture 21. Specifically, as shown in FIG. 4A or FIG. 4B, the main controller 101 controls the driving mechanism 21D to reduce the size of the opening shape of at least one of the apertures 21A and 21B of the iris aperture 21 by a predetermined step. In some embodiments, the size of the opening shape is reduced by increasing the inner diameter of at least one of the apertures 21A and 21B of the iris aperture 21. In some embodiments, the size of the opening shape is reduced by reducing the outer diameter of at least one of the apertures 21A and 21B of the iris aperture 21.

In the second example of the light receiving light amount reduction control, the main controller 101 performs control for the slit 22. Specifically, as shown in FIG. 5A or FIG. 5B, the main controller 101 controls the driving mechanism 22D to reduce the size of the aperture (slit width) of the slit 22 by a predetermined step.

In the third example of the light receiving light amount reduction control, the main controller 101 performs control for the perforated mirror 45. Specifically, the main controller 101 controls a mechanism not shown to reduce the size of the hole (aperture) formed in the perforated mirror 45 by a predetermined step.

In some embodiments, the main controller 101 performs the light receiving light amount reduction control by combining two or more of the first example to the third example described above. In some embodiments, the main controller 101 performs the light receiving light amount reduction control by any one of the first example to the third example described above, or by combining two or more of the first example to the third example described above, based on the determination result of the flare determination obtained in step S5.

(S22: Perform Involuntary Eye Movement Determination)

Next, the main controller 101 controls the involuntary eye movement determination unit 222 to determine the involuntary eye movement.

The involuntary eye movement determination unit 222 determines for the IR image whether or not the involuntary eye movement is small (large) as described above.

(S23: Is Involuntary Eye Movement Small?)

The main controller 101 judges whether or not the involuntary eye movement of the subject's eye E is small, based on the determination result obtained by performing the involuntary eye movement determination processing in step S22.

When it is judged in step S23 that the involuntary eye movement is small (S23: Y), the operation of the ophthalmic apparatus 1 proceeds to step S26. On the other hand, when it is not judged that the involuntary eye movement is small (when it is determined that the involuntary eye movement is large) (S23: N), the operation of the ophthalmic apparatus 1 proceeds to step S24.

(S24: Perform Light Amount Determination)

When it is not judged in step S23 that the involuntary eye movement is small (S23: N), the main controller 101 controls the light amount determination unit 223 to determine the light amount of the first light source 10.

The light amount determination unit 223 determines whether or not the light amount of the light output from the first light source 10 can be increased, as described above.

(S25: Can Light Amount of Light Source be Increased?)

The main controller 101 judges whether or not the light amount of the light output from the first light source 10 can be increased, based on the determination result obtained by performing the light amount of light source determination processing in step S24.

When it is judged in step S25 that the light amount of the light output from the first light source 10 can be increased (S25: Y), the operation of the ophthalmic apparatus 1 proceeds to step S27. On the other hand, when it is judged that the light amount of the light output from the first light source 10 cannot be increased (S25: N), the operation of the ophthalmic apparatus 1 proceeds to step S26.

(S26: Lengthen Imaging Time)

When it is judged in step S23 that the involuntary eye movement is small (S23: Y), or when it is judged in step S25 that the light amount of the light output from the first light source 10 cannot be increased (S25: N), the main controller 101 controls the imaging time using the image sensor 51 to be lengthened by a predetermined step.

Specifically, the main controller 101 controls the imaging time using the image sensor 51 by controlling the optical scanner 30 and the image sensor 51.

FIG. 13 shows a diagram describing an example of the control for the imaging time using the image sensor 51 in step S26. In FIG. 13, the vertical axis represents the number of pixels (number of rows) in the image sensor 51, and the horizontal axis represents time.

In the example of the control for the imaging time shown in FIG. 13, with the slit width Sw fixed, the main controller 101 controls the optical scanner 30 and the image sensor 51 to control the scanning of the irradiated region of the illumination light on the fundus Ef and the light receiving timing on the light receiving surface in the image sensor 51.

In other words, the main controller 101 can shorten the imaging time using the image sensor 51, by increasing the scan speed of the irradiated region of the illumination light on the fundus Ef (in case of changing from exposure time St1 to exposure time St0). Alternatively, the main controller 101 can lengthen the imaging time using the image sensor 51, by reducing the scan speed of the irradiated region of the illumination light on the fundus Ef (in case of changing from exposure time St0 to exposure time St1).

In step S26, the main controller 101 can lengthen the imaging time using the image sensor 51, by reducing the scan speed of the irradiated region of the illumination light on the fundus Ef.

(S27: Increase Light Amount of Light Source)

When it is judged in step S25 that the light amount of the light output from the first light source 10 can be increased (S25: Y), the main controller 101 controls the first light source 10 to increase the light amount of the light output from the first light source 10 by a predetermined incremental amount.

In other words, in step S23 to step S27, when it is judged that the involuntary eye movement is large and that there is a margin for increasing light amount in the first light source 10, the light amount of the first light source 10 is increased in step S27. On the other hand, when it is judged that the involuntary eye movement is small, or it is judged that there is not a margin for increasing light amount in the first light source 10, the imaging time using the image sensor 51 is controlled so as to lengthen in step S26.

(S28: Perform Flare Determination)

Subsequent to step S26 or step S27, the main controller 101 controls the flare determination unit 221 to perform flare determination.

The flare determination unit 221 determines whether or not the flare occurs, by analyzing the IR image that has been started to be acquired in step S2. This allows to determine whether the flare occurs in the IR image after the processing in step S26 or step S27.

(S29: Flare?)

The main controller 101 judges whether or not the flare occurs in the IR image, based on the determination result obtained by performing the flare determination processing in step S28.

When it is judged in step S29 that the flare occurs in the IR image (S29: Y), the processing of the ophthalmic apparatus 1 proceeds to step S21. On the other hand, when it is judged that the flare does not occur in the IR image (S29: N), the processing of the ophthalmic apparatus 1 terminate the processing in step S7 in FIG. 11.

As described above, the flare optimization control in step S7 in FIG. 11 is repeated until it is judged that the flare does not occur.

In step S8 in FIG. 11, the processing as shown in FIG. 14 is performed.

(S31: Light Receiving Light Amount Increasing Control)

First, the main controller 101 controls at least one of the illumination optical system 20 and the imaging optical system 40 so that the light receiving light amount of the returning light of the illumination light on the image sensor 51 is increased.

The control for the illumination optical system 20 includes control for the iris aperture 21, and control for the slit 22. The control for the imaging optical system 40 includes control for the perforated mirror 45.

In the first example of the light receiving light amount increasing control, the main controller 101 performs control for the iris aperture 21. Specifically, as shown in FIG. 4A or FIG. 4B, the main controller 101 controls the driving mechanism 21D to increase the size of the opening shape of at least one of the apertures 21A and 21B of the iris aperture 21 by a predetermined step. In some embodiments, the size of the opening shape is increased by reducing the inner diameter of at least one of the apertures 21A and 21B of the iris aperture 21. In some embodiments, the size of the opening shape is increased by increasing the outer diameter of at least one of the apertures 21A and 21B of the iris aperture 21.

In the second example of the light receiving light amount increasing control, the main controller 101 performs control for the slit 22. Specifically, as shown in FIG. 5A or FIG. 5B, the main controller 101 controls the driving mechanism 22D to increase the size of the aperture (slit width) of the slit 22 by a predetermined step.

In the third example of the light receiving light amount increasing control, the main controller 101 performs control for the perforated mirror 45. Specifically, the main controller 101 controls a mechanism not shown to increase the size of the hole (aperture) formed in the perforated mirror 45 by a predetermined step.

In some embodiments, the main controller 101 performs the light receiving light amount increasing control by combining two or more of the first example to the third example described above. In some embodiments, the main controller 101 performs the light receiving light amount increasing control by any one of the first example to the third example described above, or by combining two or more of the first example to the third example described above, based on the determination result of the flare determination obtained in step S5.

(S32: Shorten Imaging Time)

Subsequently, the main controller 101 controls the imaging time using the image sensor 51 to be shortened by a predetermined step.

Specifically, the main controller 101 controls the imaging time using the image sensor 51 by controlling at least one of the illumination optical system 20, the optical scanner 30, and the image sensor 51.

FIG. 15 shows a diagram describing an example of the control for the imaging time using the image sensor 51 in step S32. In FIG. 15, the vertical axis represents the number of pixels (number of rows) in the image sensor 51, and the horizontal axis represents time.

In the example of the control for the imaging time shown in FIG. 15, with the exposure time St fixed, the main controller 101 controls the illumination optical system 20, the optical scanner 30, and the image sensor 51 to control the scanning of the irradiated region of the illumination light on the fundus Ef and the light receiving timing on the light receiving surface in the image sensor 51.

In other words, the main controller 101 can increase the scan speed of the irradiated region of the illumination light on the fundus Ef, by controlling the slit 22 in the illumination optical system 20 to increase the slit width (in case of changing from slit width Sw1 to slit width Sw0). In this case, the main controller 101 controls the deflection angle by the optical scanner 30 and the light receiving timing in the image sensor 51, corresponding to the amount of change in the slit width. This allows to shorten the imaging time using the image sensor 51. Alternatively, the main controller 101 can reduce the scan speed of the irradiated region of the illumination light on the fundus Ef, by controlling the slit 22 in the illumination optical system 20 to reduce the slit width (in case of changing from slit width Sw0 to slit width Sw1). In this case, the main controller 101 controls the deflection angle by the optical scanner 30 and the light receiving timing in the image sensor 51, corresponding to the amount of change in the slit width. This allows to lengthen the imaging time using the image sensor 51.

In step S32, the main controller 101 can increase the scan speed of the irradiated region of the illumination light on the fundus Ef, by controlling the slit 22 in the illumination optical system 20 to increase the slit width. As a result, the imaging time using the image sensor 51 can be shortened.

(S33: Perform Flare Determination)

Subsequently, the main controller 101 controls the flare determination unit 221 to perform flare determination.

The flare determination unit 221 determines whether or not the flare occurs, by analyzing the IR image that has been started to be acquired in step S2. This allows to determine whether the flare occurs in the IR image after the processing in step S32.

(S34: Flare?)

The main controller 101 judges whether or not the flare occurs in the IR image, based on the determination result obtained by performing the flare determination processing in step S33.

When it is judged in step S34 that the flare occurs in the IR image (S34: Y), the processing of the ophthalmic apparatus 1 proceeds to step S35. On the other hand, when it is judged that the flare does not occur in the IR image (S34: N), the processing of the ophthalmic apparatus 1 proceeds to step S31.

(S35: Restore Imaging Condition Before Change)

When it is judged in step S34 that the flare occurs in the IR image (S34: Y), the main controller 101 restores the current imaging condition(s) to the imaging condition(s) before the change. In other words, the main controller 101 restores the current imaging condition(s) to the imaging condition(s) immediately prior to the time when it is judged that the flare does not occur in the IR image.

As described above, the imaging time optimization control in step S8 of FIG. 11 is repeated until it is judged that the flare occurs.

As described above, in step S6, the main controller 101 performs the flare optimization control when it is determined that the flare occurs in the IR image, and performs the imaging time optimization control when it is determined that the flare does not occur in the IR image.

In the flare optimization control, the main controller 101 changes the imaging condition(s) so as to eliminate an occurrence of the flare, by controlling at least one of the first light source 10, the illumination optical system 20, the optical scanner 30, the imaging optical system 40, and the image sensor 51. The image forming unit 210 forms the image of the fundus Ef based on the light receiving result captured by the image sensor 51 under the imaging condition(s) that has been changed by performing the flare optimization control, when it is judged in step S28 that the flare does not occur using the IR image acquired under the imaging condition(s) changed by performing the flare optimization control.

In the imaging time optimization control, the main controller 101 changes the imaging condition(s) so as to shorten the imaging time for the fundus Ef, by controlling at least one of the first light source 10, the illumination optical system 20, the optical scanner 30, the imaging optical system 40, and the image sensor 51. When it is judged in step S34 that the flare occurs using the IR image acquired under the imaging condition(s) that has been changed by performing the imaging time optimization control, the main controller 101 restores the imaging condition before the change and forms the image of the fundus Ef based on the light receiving result captured by the image sensor 51 under the imaging condition(s) under the imaging condition(s) before the change.

[Actions and Effects]

The actions and the effects of an ophthalmic apparatus, a method of controlling the same, and a program according to the embodiments will be described.

An ophthalmic apparatus (1) according to some embodiments includes a first light source (10), an illumination optical system (20), an optical scanner (30), an imaging optical system (40), an acquisition unit (the second light source 11, the half mirror 12, the illumination optical system 20, the optical scanner 30, the projection optical system 35, the imaging optical system 40, the imaging device 50, the controller 100, and the image forming unit 210), a flare determination unit (221), a controller (100, main controller 101), and an image forming unit (220). The illumination optical system is configured to generate slit-shaped illumination light using light from the first light source. The optical scanner is configured to deflect the illumination light to guide the illumination light to a fundus (Ef) of a subject's eye (E). The imaging optical system is configured to guide returning light of the illumination light from the fundus to an image sensor (51), the image sensor being configured to capture light receiving result of the returning light using a rolling shutter method, the light receiving result corresponding to an irradiated position of the illumination on the fundus. The acquisition unit is configured to acquire a fundus image (IR image) of the subject's eye using light from a second light source (11). The flare determination unit is configured to determine whether or not flare occurs, by analyzing the fundus image of the subject's eye. The controller is configured to perform flare optimization control in which an imaging condition is changed so as to eliminate an occurrence of the flare, by controlling at least one of the first light source, the illumination optical system, the optical scanner, the imaging optical system, and the image sensor based on a first determination result obtained by the flare determination unit (determination result obtained in step S5). The image forming unit is configured to form an image of the fundus based on the light receiving result captured by the image sensor, when it is determined that the flare does not occur, based on a second determination result obtained by the flare determination unit (determination result obtained in step S28) using the fundus image acquired by the acquisition unit under the imaging condition changed by performing the flare optimization control.

According to such a configuration, the imaging condition is changed so that the flare does not occur, by controlling at least one of the first light source, the illumination optical system, the optical scanner, the imaging optical system, and the image sensor. Thereby, the image of the subject's eye can be formed using the rolling shutter method in a desired imaging time. This allows to acquire the high quality images of the subject's eye while suppressing flares whose appearance differs in accordance with the subject's eye.

In some embodiments, the illumination optical system includes: a slit (22) in which a slit-shaped first aperture whose opening shape can be changed is formed, and capable of being arranged at a fundus conjugate position substantially conjugate optically to the fundus; and an iris aperture (21) in which a second aperture (apertures 21A and 21B) whose opening shape can be changed is formed, and capable of being arranged at an iris conjugate position substantially conjugate optically to an iris of the subject's eye between the first light source and the slit. The controller is configured to control the illumination optical system so as to reduce a size of the opening shape of at least one of the first aperture and the second aperture, when it is determined, based on the first determination result, that the flare occurs.

According to such a configuration, at least one of the slit and the iris aperture is controlled. Thereby, the light amount of the illumination light can be reduced with a simple configuration and a simple control. As a result, the high quality images of the subject's eye can be acquired while suppressing the occurrence of the flare.

In some embodiments, the imaging optical system includes an imaging aperture (perforated mirror 45) in which a third aperture (hole) whose opening shape can be changed is formed, and capable of being arranged at the iris conjugate position substantially conjugate optically to the iris of the subject's eye, and the controller is configured to control the imaging optical system so as to reduce a size of the opening shape of the third aperture, when it is determined, based on the first determination result, that the flare occurs.

According to such a configuration, the imaging aperture is controlled. Thereby, the light amount of the returning light of the illumination light can be reduced with a simple configuration and a simple control. As a result, the high quality images of the subject's eye can be acquired while suppressing the occurrence of the flare.

In some embodiments, the imaging aperture is a perforated mirror (45) configured to couple an optical path of the illumination optical system with an optical path of the imaging optical system, the imaging optical system being arranged in an optical axis direction passing through the third aperture, and to guide the illumination light reflected on a peripheral region of the third aperture to the fundus.

According to such a configuration, the function of the imaging aperture is implemented using the perforated mirror coupling the optical path of the illumination optical system with the optical path of the imaging optical system. Thereby, while irradiating the illumination light onto the fundus by pupil division, the configuration of the optical systems can be simplified and the high quality images of the subject's eye can be acquired.

In some embodiments, the controller is configured to repeatedly perform the flare optimization control until it is determined, based on the second determination result, that the flare does not occur.

According to such a configuration, the high quality images of the subject's eye can be acquired with a simple processing while suppressing the occurrence of the flare.

In some embodiments, the ophthalmic apparatus includes an involuntary eye movement determination unit (222) configured to determine a state of an involuntary eye movement of the subject's eye; and a light amount determination unit (223) configured to determine whether or not a light amount of light output from the first light source can be increased. The controller is configured to change the imaging condition based on a determination result obtained by the involuntary eye movement determination unit or a determination result obtained by the light amount determination unit.

According to such a configuration, the imaging condition is changed in consideration of the involuntary eye movement or the possibility of increasing the light amount of the first light source. This allows to suppress the occurrence of the flare with higher precision.

In some embodiments, the controller is configured to control at least one of the illumination optical system, the optical scanner, and the image sensor so as to lengthen an imaging time for the fundus, when it is determined by the involuntary eye movement determination unit that the involuntary eye movement is small, or when it is determined by the light amount determination unit that the light amount cannot be increased.

According to such a configuration, the illumination optical system, etc. are controlled so as to lengthen the imaging time for the fundus in accordance with the degree of the involuntary eye movement or the possibility of increasing the light amount of the first light source. This allows to acquire the high quality images of the subject's eye while reliably suppressing the occurrence of the flare whose appearance differs in accordance with the subject's eye.

In some embodiments, the controller is configured to control the first light source so as to increase the light amount, when it is determined by the involuntary eye movement determination unit that the involuntary eye movement is large and it is determined by the light amount determination unit that the light amount can be increased.

According to such a configuration, the light amount of the illumination light is increased in accordance with the degree of the involuntary eye movement or the possibility of increasing the light amount of the first light source. This allows to acquire the high quality images of the subject's eye while reliably suppressing the occurrence of the flare whose appearance differs in accordance with the subject's eye.

In some embodiments, the acquisition unit is configured to acquire the fundus image based on a light receiving result of returning light of light from the second light source captured by the image sensor.

According to such a configuration, the ophthalmic apparatus capable of acquiring the high quality images of the subject's eye with a simple configuration while suppressing the occurrence of the flare can be provided.

In some embodiments, the controller is configured to perform the flare optimization control when it is determined, based on the first determination result, that the flare occurs, and to perform imaging time optimization control in which an imaging condition is changed so as to shorten an imaging time for the fundus, by controlling at least one of the illumination optical system, the optical scanner, the imaging optical system, and the image sensor when it is determined, based on the first determination result, that the flare does not occur.

According to such a configuration, the fundus can be captured in a short imaging time when it is determined that the flare does not occur. Thereby, the high quality images of the subject's eye can be acquired.

In some embodiments, the image sensor is a CMOS image sensor.

According to such a configuration, the high quality images of the subject's eye can be acquired with a simple configuration at a low cost, while suppressing the occurrence of the flare whose appearance differs in accordance with the subject's eye.

An method of controlling an ophthalmic apparatus (1) is the method of controlling the ophthalmic apparatus including a first light source (10), an illumination optical system (20), an optical scanner (30), an imaging optical system (40), an acquisition unit (the second light source 11, the half mirror 12, the illumination optical system 20, the optical scanner 30, the projection optical system 35, the imaging optical system 40, the imaging device 50, the controller 100, and the image forming unit 210). The illumination optical system is configured to generate slit-shaped illumination light using light from the first light source. The optical scanner is configured to deflect the illumination light to guide the illumination light to a fundus (Ef) of a subject's eye (E). The imaging optical system is configured to guide returning light of the illumination light from the fundus to an image sensor (51), the image sensor being configured to capture light receiving result of the returning light using a rolling shutter method, the light receiving result corresponding to an irradiated position of the illumination on the fundus. The acquisition unit is configured to acquire a fundus image (IR image) of the subject's eye using light from a second light source (11). The method of controlling the ophthalmic apparatus includes: a first flare determination step of determining whether or not flare occurs, by analyzing the fundus image of the subject's eye; a control step of performing flare optimization control in which an imaging condition is changed so as to eliminate an occurrence of the flare, by controlling at least one of the first light source, the illumination optical system, the optical scanner, the imaging optical system, and the image sensor based on a first determination result obtained in the first flare determination step (determination result obtained in step S5); a second flare determination step of determining whether or not flare occurs, by analyzing the fundus image acquired by the acquisition unit under the imaging condition changed by performing the flare optimization control; and an image forming step of forming an image of the fundus based on the light receiving result captured by the image sensor, when it is determined, based on a second determination result obtained in the second flare determination step (determination result obtained in step S28), that the flare does not occur.

According to such a method, the imaging condition is changed so that the flare does not occur, by controlling at least one of the first light source, the illumination optical system, the optical scanner, the imaging optical system, and the image sensor. Thereby, the image of the subject's eye can be formed using the rolling shutter method in a desired imaging time. This allows to acquire the high quality images of the subject's eye while suppressing flares whose appearance differs in accordance with the subject's eye.

In some embodiments, the illumination optical system includes: a slit (22) in which a slit-shaped first aperture whose opening shape can be changed is formed, and capable of being arranged at a fundus conjugate position substantially conjugate optically to the fundus; and an iris aperture (21) in which a second aperture (apertures 21A and 21B) whose opening shape can be changed is formed, and capable of being arranged at an iris conjugate position substantially conjugate optically to an iris of the subject's eye between the first light source and the slit. The control step is performed to control the illumination optical system so as to reduce a size of the opening shape of at least one of the first aperture and the second aperture, when it is determined, based on the first determination result, that the flare occurs.

According to such a method, at least one of the slit and the iris aperture is controlled. Thereby, the light amount of the illumination light can be reduced with a simple configuration and a simple control. As a result, the high quality images of the subject's eye can be acquired while suppressing the occurrence of the flare.

In some embodiments, the imaging optical system includes an imaging aperture (perforated mirror 45) in which a third aperture (hole) whose opening shape can be changed is formed, and capable of being arranged at the iris conjugate position substantially conjugate optically to the iris of the subject's eye, and the control step is performed to control the imaging optical system so as to reduce a size of the opening shape of the third aperture, when it is determined, based on the first determination result, that the flare occurs.

According to such a method, the imaging aperture is controlled. Thereby, the light amount of the returning light of the illumination light can be reduced with a simple configuration and a simple control. As a result, the high quality images of the subject's eye can be acquired while suppressing the occurrence of the flare.

In some embodiments, the control step is performed to repeatedly perform the flare optimization control until it is determined, based on the second determination result, that the flare does not occur.

According to such a method, the high quality images of the subject's eye can be acquired with a simple processing while suppressing the occurrence of the flare.

In some embodiments, the method includes an involuntary eye movement determination step of determining a state of an involuntary eye movement of the subject's eye; and a light amount determination step of determining whether or not light output from the first light source can be increased. The control step is performed to change the imaging condition based on a determination result obtained in the involuntary eye movement determination step or a determination result obtained in the light amount determination step.

According to such a method, the imaging condition is changed in consideration of the involuntary eye movement or the possibility of increasing the light amount of the first light source. This allows to suppress the occurrence of the flare with higher precision.

In some embodiments, the control step is performed to control at least one of the illumination optical system, the optical scanner, and the image sensor so as to lengthen an imaging time for the fundus, when it is determined in the involuntary eye movement determination step that the involuntary eye movement is small, or when it is determined in the light amount determination step that the light amount cannot be increased.

According to such a method, the illumination optical system, etc. are controlled so as to lengthen the imaging time for the fundus in accordance with the degree of the involuntary eye movement or the possibility of increasing the light amount of the first light source. This allows to acquire the high quality images of the subject's eye while reliably suppressing the occurrence of the flare whose appearance differs in accordance with the subject's eye.

In some embodiments, the control step is performed to control the first light source so as to increase the light amount, when it is determined in the involuntary eye movement determination step that the involuntary eye movement is large and it is determined in the light amount determination step that the light amount can be increased.

According to such a method, the light amount of the illumination light is increased in accordance with the degree of the involuntary eye movement or the possibility of increasing the light amount of the first light source. This allows to acquire the high quality images of the subject's eye while reliably suppressing the occurrence of the flare whose appearance differs in accordance with the subject's eye.

In some embodiments, the control step is performed to perform the flare optimization control when it is determined, based on the first determination result, that the flare occurs, and to perform imaging time optimization control in which an imaging condition is changed so as to shorten an imaging time for the fundus, by controlling at least one of the illumination optical system, the optical scanner, the imaging optical system, and the image sensor when it is determined, based on the first determination result, that the flare does not occur.

According to such a method, the fundus can be captured in a short imaging time when it is determined that the flare does not occur. Thereby, the high quality images of the subject's eye can be acquired.

In some embodiments, the image sensor is a CMOS image sensor.

According to such a method, the high quality images of the subject's eye can be acquired with a simple configuration at a low cost, while suppressing the occurrence of the flare whose appearance differs in accordance with the subject's eye.

A program according to some embodiments causes a computer to execute each step of the method of controlling the ophthalmic apparatus described any one of the above.

According to such a program, the imaging condition is changed so that the flare does not occur, by controlling at least one of the first light source, the illumination optical system, the optical scanner, the imaging optical system, and the image sensor. Thereby, the image of the subject's eye can be formed using the rolling shutter method in a desired imaging time. This allows to acquire the high quality images of the subject's eye while suppressing flares whose appearance differs in accordance with the subject's eye.

The embodiments or the modification examples thereof described above are merely examples for carrying out the present invention. Those who intend to implement the present invention can apply any modification, omission, addition, or the like within the scope of the gist of the present invention.

In the above embodiments, the ophthalmic apparatus may have arbitrary functions adaptable in the field of ophthalmology. Examples of such functions include an axial length measurement function, a tonometry function, an optical coherence tomography (OCT) function, an ultrasonic inspection, and the like. It should be noted that the axial length measurement function is realized by the OCT, etc. Further, the axial length measurement function may be used to measure the axial length of the subject's eye by projecting light onto the subject's eye and detecting the returning light from the fundus while adjusting the position of the optical system in the Z direction (front-back direction) relative to the subject's eye. The intraocular pressure measurement function is realized by the tonometer, etc. The OCT function is realized by the OCT apparatus, etc. The ultrasonic inspection function is realized by the ultrasonic diagnosis apparatus, etc. Further, the present invention can also be applied to an apparatus (multifunctional apparatus) having two or more of such functions.

In some embodiments, a program for causing a computer to execute the method of controlling the ophthalmic apparatus described above is provided. Such a program can be stored in any non-transitory computer-readable recording medium. The recording medium may be an electronic medium using magnetism, light, magneto-optical, semiconductor, or the like. Typically, the recording medium is a magnetic tape, a magnetic disk, an optical disk, a magneto-optical disk, a flash memory, a solid state drive, or the like. The computer program may be transmitted and received through a network such as the Internet, LAN, etc.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in Superguide v. DIRECTV, 69 USPQ2d 1865 (Fed. Cir. 2004).

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ophthalmic apparatus, comprising:
a first light source;
an illumination optical system configured to generate slit-shaped illumination light using light from the first light source;
an optical scanner configured to deflect the illumination light to guide the illumination light to a fundus of a subject's eye;
an imaging optical system configured to guide returning light of the illumination light from the fundus to an image sensor, the image sensor being configured to capture light receiving result of the returning light using a rolling shutter method, the light receiving result corresponding to an irradiated position of the illumination on the fundus; and processing circuitry configured to acquire a fundus image of the subject's eye using light from a second light source, as an acquisition unit;

to determine whether or not flare occurs, by analyzing the fundus image of the subject's eye, as a flare determination unit;

to perform flare optimization control in which an imaging condition is changed so as to eliminate an occurrence of the flare, by controlling at least one of the first light source, the illumination optical system, the optical scanner, the imaging optical system, and the image sensor based on a first determination result obtained by the flare determination unit, as a controller; and to form an image of the fundus based on the light receiving result captured by the image sensor, when it is determined that the flare does not occur, based on a second determination result obtained by the flare determination unit using the fundus image acquired by the acquisition unit under the imaging condition changed by performing the flare optimization control, as an image forming unit, wherein the imaging optical system includes an imaging aperture in which a third aperture whose opening shape can be changed is formed, and capable of being arranged at the iris conjugate position substantially conjugate optically to the iris of the subject's eye, and the controller is configured to control the imaging optical system so as to reduce a size of the opening shape of the third aperture, when it is determined, based on the first determination result, that the flare occurs.

2. The ophthalmic apparatus of claim 1, wherein the illumination optical system includes:

a slit in which a slit-shaped first aperture whose opening shape can be changed is formed, and capable of being arranged at a fundus conjugate position substantially conjugate optically to the fundus; and an iris aperture in which a second aperture whose opening shape can be changed is formed, and capable of being arranged at an iris conjugate position substantially conjugate optically to an iris of the subject's eye between the first light source and the slit, and the controller is configured to control the illumination optical system so as to reduce a size of the opening shape of at least one of the first aperture and the second aperture, when it is determined, based on the first determination result, that the flare occurs.

3. The ophthalmic apparatus of claim 1, wherein the imaging aperture includes a perforated mirror configured to couple an optical path of the illumination optical system with an optical path of the imaging optical system, the imaging optical system being arranged in an optical axis direction passing through the third aperture, and to guide the illumination light reflected on a peripheral region of the third aperture to the fundus.

4. The ophthalmic apparatus of claim 1, wherein the controller is configured to repeatedly perform the flare optimization control until it is determined, based on the second determination result, that the flare does not occur.

5. The ophthalmic apparatus of claim 1, wherein:

the processing circuitry is further configured as an involuntary eye movement determination unit configured to determine a state of an involuntary eye movement of the subject's eye; and the processing circuitry is further configured as a light amount determination unit configured to determine whether or not a light amount of light output from the first light source can be increased, wherein the controller is configured to change the imaging condition based on a determination result obtained by the involuntary eye movement determination unit or a determination result obtained by the light amount determination unit.

6. The ophthalmic apparatus of claim 5, wherein the controller is configured to control at least one of the illumination optical system, the optical scanner, and the image sensor so as to lengthen an imaging time for the fundus, when it is determined by the involuntary eye movement determination unit that the involuntary eye movement is small, or when it is determined by the light amount determination unit that the light amount cannot be increased.

7. The ophthalmic apparatus of claim 5, wherein the controller is configured to control the first light source so as to increase the light amount, when it is determined by the involuntary eye movement determination unit that the involuntary eye movement is large and it is determined by the light amount determination unit that the light amount can be increased.

8. The ophthalmic apparatus of claim 1, wherein the acquisition unit is configured to acquire the fundus image based on a light receiving result of returning light of light from the second light source captured by the image sensor.

9. The ophthalmic apparatus of claim 1, wherein the controller is configured to perform the flare optimization control when it is determined, based on the first determination result, that the flare occurs, and to perform imaging time optimization control in which an imaging condition is changed so as to shorten an imaging time for the fundus, by controlling at least one of the illumination optical system, the optical scanner, the imaging optical system, and the image sensor when it is determined, based on the first determination result, that the flare does not occur.

10. The ophthalmic apparatus of claim 1, wherein the image sensor includes a CMOS image sensor.

11. An method of controlling an ophthalmic apparatus comprising:

a first light source; and an illumination optical system configured to generate slit-shaped illumination light using light from the first light source;

an optical scanner configured to deflect the illumination light to guide the illumination light to a fundus of a subject's eye;

an imaging optical system configured to guide returning light of the illumination light from the fundus to an image sensor, the image sensor being configured to capture light receiving result of the returning light, the light receiving result corresponding to an irradiated position of the illumination on the fundus; and processing circuitry configured as an acquisition unit configured to acquire a fundus image of the subject's eye using light from a second light source, the method comprising:

a first flare determination step of determining whether or not flare occurs, by analyzing the fundus image of the subject's eye;

a control step of performing flare optimization control in which an imaging condition is changed so as to eliminate an occurrence of the flare, by controlling at least one of the first light source, the illumination optical system, the optical scanner, the imaging optical system, and the image sensor based on a first determination result obtained in the first flare determination step;

a second flare determination step of determining whether or not flare occurs, by analyzing the fundus image acquired by the acquisition unit under the imaging condition changed by performing the flare optimization control; and an image forming step of forming an image of the fundus based on the light receiving result captured by the image sensor, when it is determined, based on a second determination result obtained in the second flare determination step, that the flare does not occur, wherein the imaging optical system includes an imaging aperture in which a third aperture whose opening shape can be changed is formed, and capable of being arranged at the iris conjugate position substantially conjugate optically to the iris of the subject's eye, and the control step is performed to control the imaging optical system so as to reduce a size of the opening shape of the third aperture, when it is determined, based on the first determination result, that the flare occurs.

12. The method of controlling the ophthalmic apparatus of claim 11, wherein the illumination optical system includes:

a slit in which a slit-shaped first aperture whose opening shape can be changed is formed, and capable of being arranged at a fundus conjugate position substantially conjugate optically to the fundus; and an iris aperture in which a second aperture whose opening shape can be changed is formed, and capable of being arranged at an iris conjugate position substantially conjugate optically to an iris of the subject's eye between the first light source and the slit, and the control step is performed to control the illumination optical system so as to reduce a size of the opening shape of at least one of the first aperture and the second aperture, when it is determined, based on the first determination result, that the flare occurs.

13. The method of controlling the ophthalmic apparatus of claim 11, wherein the control step is performed to repeatedly perform the flare optimization control until it is determined, based on the second determination result, that the flare does not occur.

14. The method of controlling the ophthalmic apparatus of claim 11, further comprising:

an involuntary eye movement determination step of determining a state of an involuntary eye movement of the subject's eye; and a light amount determination step of determining whether or not light output from the first light source can be increased, wherein the control step is performed to change the imaging condition based on a determination result obtained in the involuntary eye movement determination step or a determination result obtained in the light amount determination step.

15. The method of controlling the ophthalmic apparatus of claim 14, wherein the control step is performed to control at least one of the illumination optical system, the optical scanner, and the image sensor so as to lengthen an imaging time for the fundus, when it is determined in the involuntary eye movement determination step that the involuntary eye movement is small, or when it is determined in the light amount determination step that the light amount cannot be increased.

16. The method of controlling the ophthalmic apparatus of claim 14, wherein the control step is performed to control the first light source so as to increase the light amount, when it is determined in the involuntary eye movement determination step that the involuntary eye movement is large and it is determined in the light amount determination step that the light amount can be increased.

17. The method of controlling the ophthalmic apparatus of claim 11, wherein the control step is performed to perform the flare optimization control when it is determined, based on the first determination result, that the flare occurs, and to perform imaging time optimization control in which an imaging condition is changed so as to shorten an imaging time for the fundus, by controlling at least one of the illumination optical system, the optical scanner, the imaging optical system, and the image sensor when it is determined, based on the first determination result, that the flare does not occur.

18. The method of controlling the ophthalmic apparatus of claim 11, wherein the image sensor includes a CMOS image sensor.

19. A non-transitory computer readable recording medium storing a program of causing a computer to execute each step of the method of controlling the ophthalmic apparatus of claim 11.

* * * * *